United States Patent [19]

Takigawa et al.

[11] Patent Number: 4,564,477
[45] Date of Patent: Jan. 14, 1986

[54] POLYPRENYL COMPOUNDS AND METHOD OF PRODUCING THE SAME

[75] Inventors: Tetsuo Takigawa; Koichi Ibata; Masafumi Okada; Masao Mizuno; Takashi Nishida, all of Kurashiki, Japan

[73] Assignee: Kuraray Co., Ltd., Kurashiki, Japan

[21] Appl. No.: 467,253

[22] Filed: Feb. 17, 1983

[30] Foreign Application Priority Data

| Feb. 19, 1982 | [JP] | Japan | 57-26300 |
| Mar. 18, 1982 | [JP] | Japan | 57-44256 |
| Mar. 19, 1982 | [JP] | Japan | 57-44839 |
| Mar. 24, 1982 | [JP] | Japan | 57-47658 |
| Mar. 29, 1982 | [JP] | Japan | 57-51903 |
| Mar. 29, 1982 | [JP] | Japan | 57-51904 |
| Apr. 6, 1982 | [JP] | Japan | 57-57863 |
| May 14, 1982 | [JP] | Japan | 57-82040 |
| May 24, 1982 | [JP] | Japan | 57-88320 |
| Jun. 2, 1982 | [JP] | Japan | 57-95119 |

[51] Int. Cl.$^4$ .......... C07C 49/203; C09F 5/00
[52] U.S. Cl. .......... 260/405.5; 260/465.9; 260/404; 260/404.5; 568/410; 568/412; 568/417; 568/448; 564/204; 564/207; 564/509; 564/511; 564/271
[58] Field of Search ........... 568/410, 412, 417, 448; 260/465.9, 405.5, 404, 404.5; 564/204, 207, 509, 511, 271, 277

[56] References Cited

U.S. PATENT DOCUMENTS

| 3,326,978 | 6/1967 | Dunkel | 568/417 |
| 4,116,955 | 9/1978 | Ichikawa et al. | 568/410 |
| 4,386,227 | 5/1983 | Sato et al. | 260/405.5 |

OTHER PUBLICATIONS

Hemming, Chem. Abst., vol. 99, #171383, (1983).
"Dolichol: A Naturally Occurring Isoprenoik Alcohol", Pennock et al.
"The High-Performance Liquid-Chromatographic Analysis of Ficaprenol and Dolichol", Keenan et al.
"Effect of Exogeneous Dolichyl Monophosphate on a Developmental Change in Mannosylphosphoryldolichol Biosynthesis", Harford et al.
"The Tissue and Subcellular Districution of [$^3$H]Dolichol in the Rat", Keenan et al.
"Metabolism of Lipid Intermediate in Biosynthesis of Glycoprotein of Regenerated Liver", Hara et al.
"Dolichol: A Naturally-Occurring C$_{100}$ Isoprenoid Alcohol", Burgos et al.
"Polyisoprenols in Pinus Sylvestris Needles", Hannus.
"Terpenoids of Pinus Strobus Cortex Tissue", Zinkel et al.
"Synthese Du Squalene Par Couplage Queue a Queue", Biellmann et al.
"Desulfonylation of Aryl Alkyl Sulfones", Trost et al.

Primary Examiner—James H. Reamer
Attorney, Agent, or Firm—Burns, Doane, Swecker & Mathis

[57] ABSTRACT

There are provided polyprenyl compounds of the formula

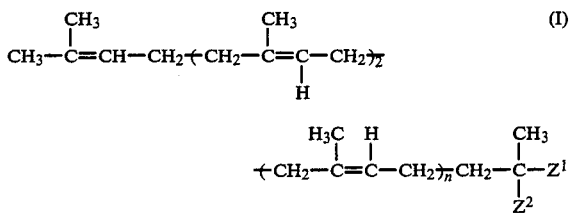

wherein

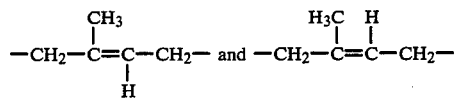

represent a trans-isoprene unit and a cis-isoprene unit, respectively, n is an integer of 11-19, $Z^1$ and $Z^2$ combinedly represent =O, =CH—COOH, =CH—COOR$^1$, =CH—CN, =C(CN)COOR$^2$, =CH—CO—NH$_2$, =CH—CO—N(R$^3$) (R$^4$), =CH—CO—NHR$^5$, =CH—CH$_2$—N(R$^3$) (R$^4$), =CH—CH$_2$—NHR$^5$ or =CH—CHO or $Z^1$ is a hydrogen atom and $Z^2$ is —CH$_2$COOH, —CH$_2$COOR$^6$, —CH(CN)COOR$^2$, —CH$_2$CN, —CH$_2$—CO—NH$_2$, —CH=CH—N(R$^3$) (R$^4$) or —CH$_2$—CH=N—R$^5$, R$^1$, R$^2$ and R$^6$ each being a lower alkyl group, R$^3$ and R$^4$ each independently being a lower-alkyl, cycloalkyl, aryl or aralkyl group or R$^3$ and R$^4$ combinedly representing an alkylene group containing 2-5 carbon atoms, and R$^5$ being a lower-alkyl, cycloalkyl, aryl or aralkyl group. These polyprenyl compounds can be synthesized starting with a polyprenol obtainable from leaves of a plant such as *Ginkgo biloba* or *Cedrus deodara* by extraction and as necessary followed by hydrolysis, or a reactive derivative thereof. The polyprenyl compounds are useful as intermediates for the synthesis of dolichol without the use of an expensive C$_5$ chain extender.

10 Claims, No Drawings

POLYPRENYL COMPOUNDS AND METHOD OF PRODUCING THE SAME

BACKGROUND OF THE INVENTION

1. Field of the Invention

This invention relates to novel polyprenyl compounds and methods of producing the same. More particularly, it relates to novel polyprenyl compounds which are useful as intermediates for the synthesis of mammalian dolichols and methods of producing the same.

2. Description of the Prior Art

Dolichol was first isolated in 1960 from human kidney and animal tissues such as ox kidney, pig kidney, pig heart, pig liver and rat liver by J. F. Pennock et al. [see Nature (London), 186, 470(1960)]. Later, it was revealed that dolichol is a mixture of polyprenol homologs having the general formula

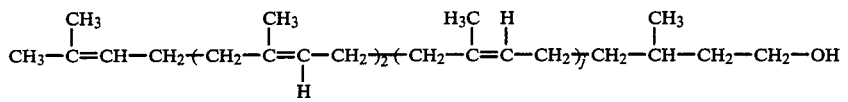

wherein

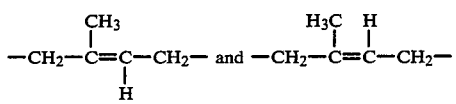

represent a trans-isoprene unit and a cis-isoprene unit, respectively (the same definition shall apply throughout the present specification), and the number j of cis-isoprene units in the above formula is generally distributed between 12 to 18 and three homologs in which j is 14, 15 and 16 are present in major proportions [R. W. Keenan et al., Biochemical Journal, 165, 405 (1977)]. It is also known that dolichol is widely distributed in mammals, and performs a very important function in maintaining the lives of organisms. For example, J. B. Harford et al. showed by in vitro tests using the calf or pig brain white matter that exogenous dolichol enhances incorporation of carbohydrates such as mannose into lipid, and consequently increases the formation of glycoproteins which are important for maintaining the lives of organisms [Biochemical and Biophysical Research Communications, 76,1036 (1977)]. Since the effect of dolichol to incorporate carbohydrates into lipid is remarkable in mature animals as compared with those in the actively growing stage, the action of dolichol has attracted attention for its possible prevention of aging.

R. W. Keenan et al. state that it is important for organisms which rapidly keep growing, for example, those in the infant stage, to take dolichols extraneously so as to supplement the dolichol produced by biosynthesis within their own body [Archives of Biochemistry and Biophysics, 179, 634 (1977)].

Akamatsu et al. determined the quantity of dolichol phosphate in the regenerated liver of a rat and found that the quantity determined is much smaller than that in normal liver and the function of the liver tissues to synthesize glycopropteins is drastically reduced and that the addition of exogenous dolichol phosphate improves the reduced function of glycoprotein synthesis (reported at the 1981 Conference of the Japanese Society of Biochemistry).

In this way, dolichol is a very important substance for organisms, and it is strongly desired to develop its use as a medicine or an intermediate for the production of medicines, cosmetics, etc.

However, it is not easy to isolate dolichol from mammalian tissues. For example, only about 0.6 g at most of dolichol can be obtained from 10 kg of pig liver through complicated separating procedures [See J. Burgos et al., Biochemical Journal, 88, 470 (1963)].

On the other hand, it is extremely difficult by the present day techniques of organic synthesis to produce dolichol by a wholly synthetic process, as can be seen in the light of the complex and unique molecular structure.

It is so far known that polyprenols of the general formula

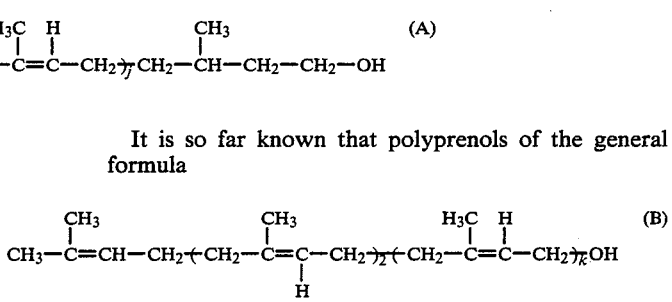

wherein k=4 to 6, which are called betulaprenols, can be isolated from *Betula verrucola*. However, the betulaprenols so far known contain up to six cis-isoprene units at most, and in order to synthesize dolichol containing homologs having 14, 15 and 16 cis-isoprene units respectively as major components from these betulaprenols, it is necessary to link at least 8 isoprene units while maintaining them in cis-form. This procedure is almost impossible by the present-day organic synthetic techniques.

K. Hannus et al. reported that a polyisoprenyl fraction in an amount of about 1% dry weight was isolated from the needles of *Pinus sylvestris*, and the fraction consisted of polyisoprenyl acetates with 10 to 19 isoprene units predominantly in the cis-configuration [Phytochemistry, 13, 2563 (1974)]. However, their report does not explain the details of the trans and cis configurations in said polyprenyl acetates. Furthermore, according to a report of D. F. Zinkel et al., a $C_{90}$ polyprenol containing 18 isoprene units or a homologous series of polyprenols averaging 18 isoprene units is present in *Pinus strobus* needle extracts [cf. Phytochemistryl, 11, 3387 (1972)]. However, this report does not contain any detailed analysis of the trans and cis configurations in said polyprenol.

Part of the present inventors, together with their colleagues, previously found that extraction of the leaves of *Ginkgo biloba* and *Cedrus deodara* followed by an adequate separation procedure, such as chromatography or fractional dissolution, if necessary following hydrolysis, gives a polyprenyl fraction composed of a mixture of polyprenols and/or acetates thereof which contain 14–22 isoprene units in quite the same trans/cis configurations as in mammalian dolichols and that said polyprenyl fraction is very similar in the distribution of polyprenyl homologs to mammalian dolichols, the only difference being the absence in said fraction of the alpha-terminal saturated isoprene unit and that said polyprenyl fraction, if desired, can be separated relatively easily into the individual constituent polyprenyl homologs (each being homogeneous with respect to the number of isoprene units), and proposed a method of producing dolichols or precursors thereof which comprises reacting such polyprenyl compound or fraction or a reactive derivative thereof with a Grignard reagent or lithium compound derived from a 4-hydroxy-2-methylbutyl halide or a functional precursor thereof (EP No. 0 054 753 A1 published on June 30, 1982; U.S. patent application Ser. No. 371,487 which is a continuation-in-part of U.S. patent application Ser. No. 324,636 filed on Nov. 24, 1981, now abandoned). However, this method is disadvantageous in that a 4-hydroxy-2-methylbutyl halide or a functional precursor thereof, which is expensive, is required; the method should desirably be improved.

SUMMARY OF THE INVENTION

An object of the invention is to provide novel polyprenyl compounds useful as the intermediates for the production of dolichols by a method distinct from the previously proposed method cited above.

Another object of the invention is to provide novel polyprenyl compounds which are useful as intermediates for the synthesis of dolichols without necessity of the use of such an expensive $C_5$ chain extender as a 4-hydroxy-2-methylbutyl halide or a functional precursor thereof.

To accomplish these objects and other objects which will become apparent from the description which follows, the present invention provides polyprenyl compounds represented by the general formula

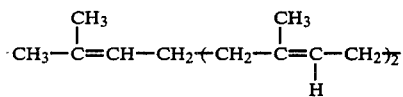
(I)

-continued

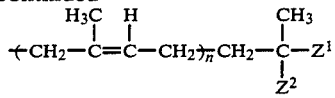

wherein

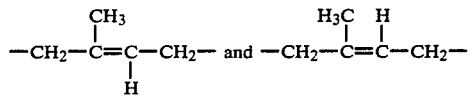

represent a trans-isoprene unit and a cis-isoprene unit, respectively, n is an integer of 11 to 19, and $Z^1$ and $Z^2$ combinedly represent =O, =CH—COOH, =CH—COOR$^1$, =CH—CN, =C(CN)COOR$^2$, =CH—CO—NH$_2$, =CH—CO—N(R$^3$)(R$^4$), =CH—CO—NHR$^5$, =CH—CH$_2$—N(R$^3$)(R$^4$), =CH—CH$_2$—NHR$^5$ or =CH—CHO or $Z^1$ is a hydrogen atom and $Z^2$ is —CH$_2$COOH, —CH$_2$COOR$^6$, —CH(CN)COOR$^2$, —CH$_2$CN, —CH$_2$—CO—NH$_2$, —CH=CH—N(R$^3$)(R$^4$) or —CH$_2$—CH=N—R$^5$, R$^1$, R$^2$ and R$^6$ each being a lower alkyl group, R$^3$ and R$^4$ each being independently a lower-alkyl, cycloalkyl, aryl or aralkyl group or R$^3$ and R$^4$ combinedly representing an alkylene group containing 2 to 5 carbon atoms, and R$^5$ being a lower-alkyl, cycloalkyl, aryl or aralkyl group.

These polyprenyl compounds can easily be produced using a polyprenyl halide, which is derivable from the above-mentioned polyprenol obtained from leaves of a plant such as *Ginkgo biloba* or *Cedrus deodara*, an acetoacetate ester, which is relatively unexpensive, and, as necessary, other reagents. These polyprenyl compounds can be converted to dolichols via one or more reaction steps and therefore are useful as intermediates for dolichol synthesis. These polyprenyl compounds can also be used for the synthesis of dolichol analogs and various other polyprenyl compounds by taking advantage of their functional terminal groups.

DETAILED DESCRIPTION OF THE INVENTION

The polyprenyl compounds which can be provided by the present invention include the following:

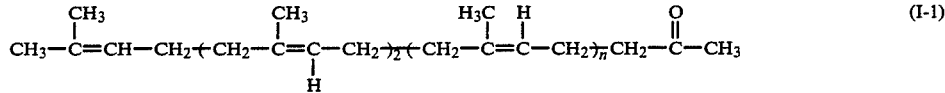
(I-1)

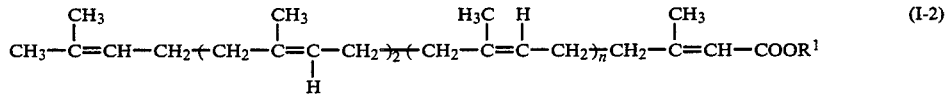
(I-2)

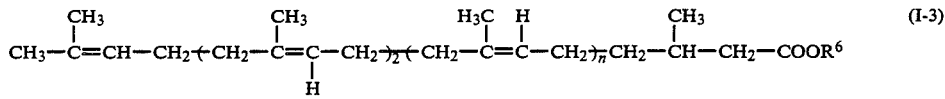
(I-3)

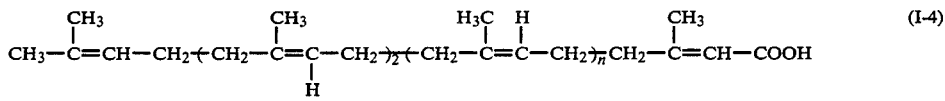
(I-4)

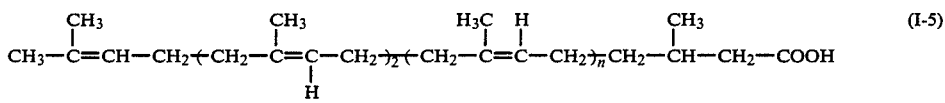
(I-5)

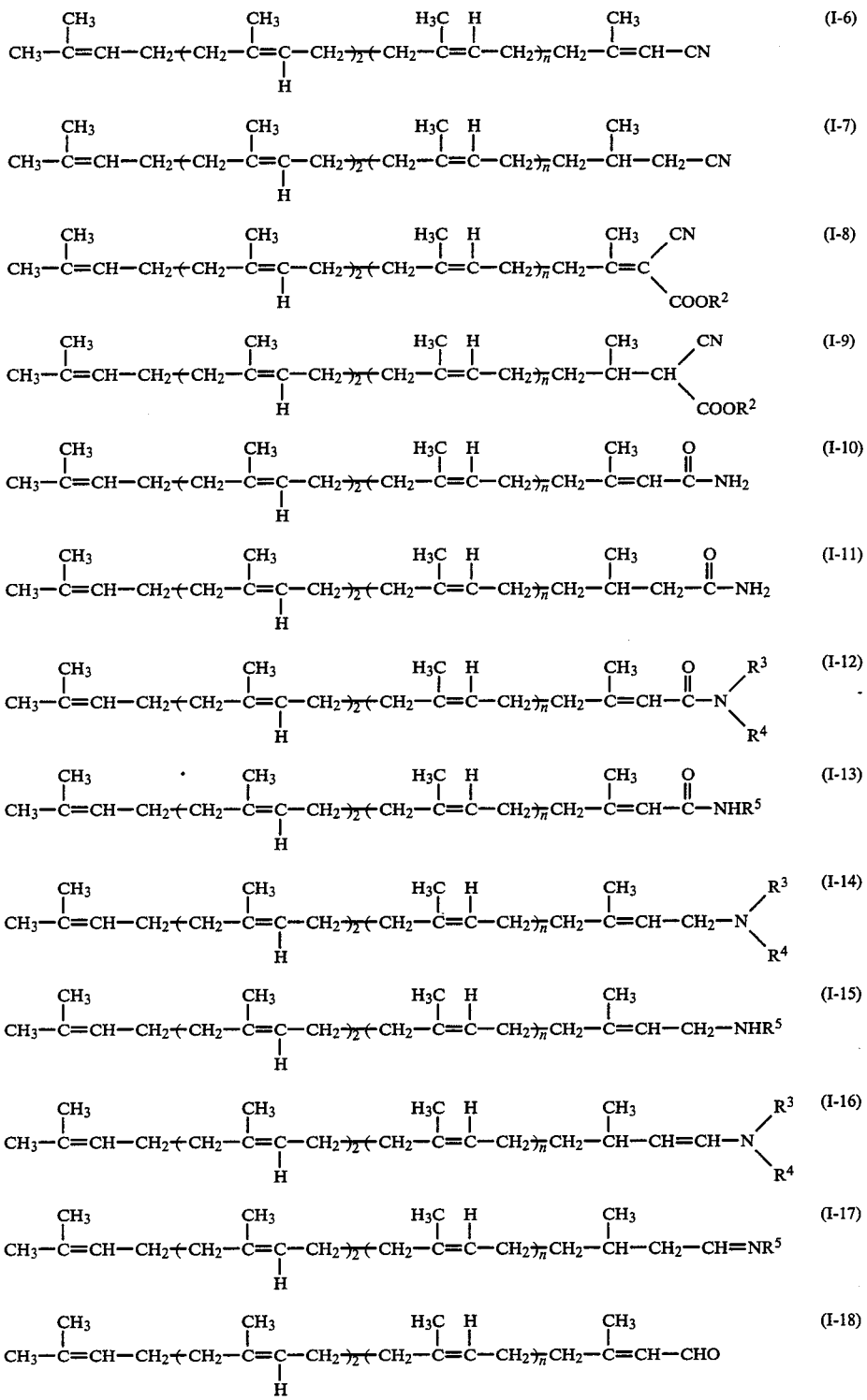

In the above formulas,

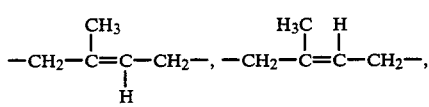

n, $R^1$, $R^2$, $R^3$, $R^4$, $R^5$ and $R^6$ are as defined above. $R^1$, $R^2$ and $R^6$ each may be an alkyl group containing 1 to 6 carbon atoms, such as methyl, ethyl, n-propyl, isopropyl, n-butyl, isobutyl, tert-butyl, n-pentyl, neopentyl or n-hexyl, and preferably is an alkyl group containing 1 to 4 carbon atoms. $R^3$ and $R^4$ each may independently be an alkyl group containing 1 to 4 carbon atoms such as methyl, ethyl, n-propyl, isopropyl or n-butyl; a cycloalkyl group containing 5 to 10 carbon atoms, such as cyclopentyl, cyclohexyl or methylcyclohexyl; an aryl group containing 6 to 10 carbon atoms, such as phenyl, tolyl or naphthyl; or an aralkyl group containing 7 to 10 carbon atoms, such as benzyl or phenethyl. Furthermore, $R^3$ and $R^4$ may combinedly represent an alkylene group containing 2 to 5 carbon atoms, such as —(CH$_2$)$_2$—, —(CH$_2$)$_3$—, —CH(CH$_3$)—CH$_2$—, —(CH$_2$)$_4$—, —CH$_2$—CH(CH$_3$)—CH$_2$—, —(CH$_2$)$_5$— or —CH$_2$—C(CH$_3$)$_2$—CH$_2$—. $R^5$ is a lower-alkyl, cycloalkyl, aryl or aralkyl group such as mentioned above for $R^3$ and $R^4$.

The polyprenyl compound of formula (I-1) [hereinafter referred to as "polyprenylacetone (I-1)"] can be produced by reacting a polyprenyl halide of the formula

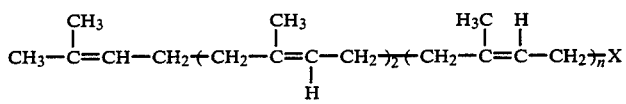

wherein X is a halogen atom, and

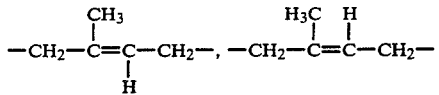

and n are as defined above, with an acetoacetic acid ester of the formula

 (III)

wherein $R^7$ is a lower alkyl group [said ester being hereinafter referred to as "acetoacetate (III)"], in the presence of a basic compound and saponifying and decarboxylating the resulting compound of the formula

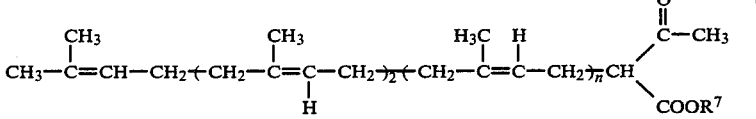

wherein

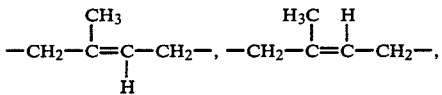

n and $R^7$ are as defined above.

The polyprenyl halide (II) can easily be produced by halogenating a polyprenol of the formula

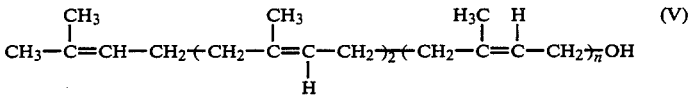 (V)

wherein

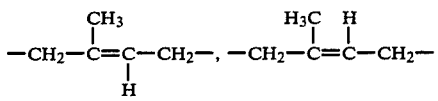

and n are as defined above, or a mixture thereof, which can be obtained, as mentioned above, from *Ginkgo biloba* or *Cedrus deodara* extracts either directly or via hydrolysis, with a halogenating agent such as a phosphorus trihalide (e.g. PCl$_3$, PBr$_3$) or a thionyl halide (e.g. SOCl$_2$, SOBr$_2$). The halogenation reaction is generally carried out by dissolving the above polyprenol in an appropriate solvent such as, for example, hexane or diethyl ether, and adding thereto the halogenating agent at about $-20°$ C. to $+50°$ C. in the presence or absence of a base, typically triethylamine or pyridine, for instance.

In formula (III), $R^7$ may be a lower alkyl group such as methyl, ethyl, n-propyl, isopropyl or n-butyl.

The reaction of polyprenyl halide (II) with acetoacetate (III) is preferably carried out in a solvent. Suitable examples of the solvent are ether-type solvents such as diethyl ether, tetrahydrofuran, dioxane and dimethoxyethane. The amount of the solvent is not critical but is 2–100 times (by weight), preferably 5–80 times (by weight), more preferably 10–50 times (by weight) the amount of polyprenyl halide (II). For the desired reaction, it is preferable that the solvent is adequately dried. The presence of a basic compound is essential to the reaction. Suitable examples of basic compound are alkali metal hydrides, hydroxides and alkoxides, such as sodium hydride, potassium hydride, sodium hydroxide, potassium hydroxide, sodium tert-butoxide, potassium tert-butoxide, sodium methoxide and sodium ethoxide, and further n-butyllithium and methyllithium. The basic compound is used in an amount of about 0.1–5.0 moles, preferably 0.5–3.0 moles, more preferably 0.7–1.5 moles, per mole of acetoacetate (III). In a preferred embodiment, an acetoacetate anion is first formed either by adding the acetoacetate (III) to a solution or dispersion of the basic compound or, alternatively, by adding the basic compound all at once or portionwise to a solution of acetoacetate (III) and then the reaction is carried out by adding thereto the polyprenyl halide (II). The molar ratio of acetoacetate (III) to polyprenyl halide (II) is not critical but the acetoacetate (III)/polyprenyl halide (II) molar ratio is 1/2 to 20/1, preferably 4/5 to 10/1, more preferably 1/1 to 5/1. The anion formation from acetoacetate (III) is desirably carried out in an inert gas atmosphere, such as nitrogen or argon, at a temperature of $-30°$ C. to $+100°$ C., preferably $-10°$ C. to $+80°$ C., whereby the desired anion can be formed in a smooth manner while side reactions are inhibited. The time required for this anion formation depends on the reaction temperature but generally about 10 minutes to about 5 hours is sufficient for the purpose. The polyprenyl halide (II) is added to the thus-prepared solution of acetoacetate (III) anion. Depending on the reaction conditions employed, the polyprenyl halide (II) is added all at once or in several portions or dropwise for the smooth reaction. The reaction temperature at the time of the addition of polyprenyl halide (II) and during the subsequent period until the reaction is over is not critical but preferably is in the range of from $-10°$ C. to the boiling point of the solvent used. If the reaction temperature is too low, the reaction proceeds slowly and too much time is required for the completion of the reaction. On the contrary, if the reaction temperature is too high, undesirable side reactions proceed. From this viewpoint, it is preferable to use a reaction temperature within the range of $0°$ C. to $80°$ C. For completion of the reaction following the addition of polyprenyl halide (II), it is necessary to continue the stirring of the reaction mixture at the above temperature. The time required for said stirring depends on the reaction temperature employed but generally is about 30 minutes to about 24 hours. The progress of the reaction can conveniently and preferably be confirmed by tracing the decrease of the starting polyprenyl halide (II) by thin layer chromatography.

After the reaction, the compound of formula (IV) can easily be isolated from the reaction mixture and purified by any of the so far known isolation/purification methods used in organic syntheses. In particular, chromatography is a convenient method. Usable chromatography adsorbents are, for instance, silica gel, alumina, activated carbon and cellulose. Among them, silica gel is especially suited for the purpose. A mixture of a hydrocarbon solvent, such as hexane, pentane, petroleum ether, benzene or toluene, and a small amount of a polar solvent, such as diethyl ether, diisopropyl ether, chloroform, methylene chloride, methyl acetate, ethyl acetate, acetone, ethyl alcohol or isopropyl alcohol, is suitable as the developing solvent. Hereinafter it is to be understood that, unless otherwise stated, the above-mentioned adsorbents and the above-mentioned developing solvents can be used effectively in isolation and purification using chromatography.

It is also possible to omit the isolation/purification step, namely to perform the next polyprenylacetone (I-1) synthesis reaction directly and then carry out a purification step.

The compound of formula (IV) can be saponified by any of the saponification methods so far used for the saponification of higher fatty acid esters. Thus, for example, the compound of formula (IV) can be saponified by stirring the same together with sodium hydroxide or potassium hydroxide in aqueous methanol, aqueous ethanol or aqueous isopropanol. Sodium hydroxide or potassium hydroxide is desirably used in an amount of about 1.0-20.0 mole equivalents, preferably 1.5-10.0 mole equivalents, based on the compound of formula (IV). Suitable reaction solvents are aqueous alcohols such as mentioned above. Addition of a small amount of a hydrocarbon solvent such as hexane, pentane, benzene or toluene is also preferable for the purpose of increasing the solubility of the compound of formula (IV). For smooth progress of the above saponification reaction, it is desirable to use a reaction temperature of from $0°$ C. to the boiling point of the solvent used, preferably a temperature within the range of $25°$-$65°$ C. The time required for the completion of the reaction depends on the temperature conditions employed but generally is in the range of about 0.5-24 hours.

After the saponification reaction is carried out in the above manner, the reaction mixture, preferably under room temperature or ice cooling conditions, is neutralized with a mineral acid such as hydrochloric acid or sulfuric acid and further made acidic to a pH value of about 1-3, whereupon the decarboxylation reaction spontaneously occurs to give the polyprenylacetone (I-1), which is one of the compounds of the present invention. When the decarboxylation reaction is completed, the reaction mixture is extracted with hexane, benzene or diethyl ether, for instance, the organic layer is washed sufficiently with water and then dried and the solvent is distilled off to give the desired polyprenylacetone (I-1) in a crude form. Chromatography is suitably used for purifying the product.

The polyprenylacetone (I-1) is one of the most important compounds among the compounds of the present invention. All of the other polyprenyl compounds of the invention can be derived from this polyprenylacetone (I-1).

The compound of formula (I-2) [hereinafter referred to as "polyprenylcarboxylate (I-2)"] can be produced from the polyprenylacetone (I-1) and a compound of the formula

wherein $R^1$ and $R^8$ each is a lower alkyl group, by the Wittig reaction.

The Wittig reaction of polyprenylacetone (I-1) and the compound of formula (VI) is generally carried out in a solvent. Suitable examples of the solvent are dimethylformamide, tetrahydrofuran, diethyl ether and benzene. For the desired reaction, it is preferable that the solvent is sufficiently dried. From the same viewpoint, the reaction should desirably be carried out under an inert gas such as nitrogen or argon. The amount of the solvent is not critical but generally the solvent is used in an amount of about 5-50 parts by weight, preferably 10-30 parts by weight, per part by weight of polyprenylacetone (I-1). Especially preferred examples of the compound of formula (VI) (Wittig reagent) are:

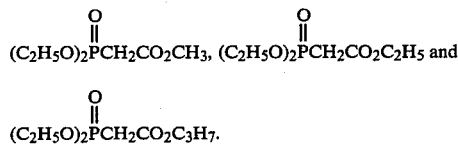

In the Wittig reaction, it is required to treat the above Wittig reagent with a basic compound for forming a phosphoylide. Suitable basic compounds for this purpose are, for example, n-butyllithium, methyllithium, sodium hydride, potassium hydride, sodium methoxide and sodium ethoxide. After addition of such a basic compound to the above-mentioned solvent, the above Wittig reagent is added dropwise with stirring at a temperature of about −30° C. to about +80° C., preferably −10° C. to +50° C. After completion of the dropwise addition, stirring is continued at a temperature within the same range as mentioned above for about 0.5 to about 24 hours to complete the phosphoylide formation. The basic compound is preferably used in an amount of about 0.5–1.5 mole equivalents, based on the Wittig reagent. The polyprenylacetone (I-1) is added to the phosphoylide solution and the reaction is allowed to proceed at about 0° C. to about 100° C., preferably at 15° C. to 80° C., to give the polyprenylcarboxylate (I-2). The time required for the completion of this reaction is within the range of about 0.5 to about 24 hours. The Wittig reagent is used in an amount of 0.5–10.0 mole equivalents, preferably 0.8–8.0 mole equivalents, more preferably 1.0–5.0 mole equivalents, based on the polyprenylacetone (I-1).

The polyprenylcarboxylate (I-2) synthesized in the above manner can be subjected, if necessary, to the ester exchange reaction so as to exchange the alcohol residue thereof for another lower alcohol residue. Hydrolysis of polyprenylcarboxylate (I-2) by a method generally applicable to hydrolysis of known fatty acid esters can give the compound of formula (I-4) [hereinafter referred to as "polyprenylcarboxylic acid (I-4)"]. Thus, for instance, stirring of the polyprenylcarboxylate (I-2) together with about 2–5 moles, per mole of said polyprenylcarboxylate (I-2), of sodium hydroxide in aqueous ethanol under refluxing conditions for about 1–5 hours can give the polyprenylcarboxylic acid (I-4) in high yield.

The polyprenylcarboxylate (I-2) and polyprenylcarboxylic acid (I-4) can be purified according to a variety of known isolation/purification methods, especially chromatography which is simple and convenient.

The polyprenylcarboxylic acid (I-4), when subjected to selective hydrogenation of the carbon-carbon double bond on the carboxyl terminal side with hydrogen ($H_2$) in the presence of a hydrogenation catalyst or to reduction using lithium in liquid ammonia [Birch reduction], can be converted to the compound of formula (I-5) [hereinafter referred to as "dihydropolyprenylcarboxylic acid (I-5)"]. The dihydropolyprenylcarboxylic acid (I-5), when esterified, can be converted to the compound of formula (I-3).

In carrying out the above hydrogenation reaction, the use of too severe hydrogenation conditions is undesirable Since hydrogenation occurs on other double bonds as well as carbon-carbon double bond on the carboxyl terminal side. On the contrary, the use of too mild conditions is also undesirable since the desired reaction does not proceed at all or too much time is required for the completion of the reaction. It is important to select, from the above viewpoint, the adequate reaction conditions for conducting the hydrogenation reaction in a favorable manner. Usable hydrogenation catalysts are metals, such as rhodium, palladium and nickel, and compounds thereof. Among them, rhodium complexes are preferable, for example, $RhCl[P(C_6H_5)_3]_3$, $HRhCl_2[P(C_6H_5)_3]_3$ or a complex prepared from $Rh_2(1,5\text{-cyclooctadiene})_2Cl_2$ and menthyldiphenylphosphine or neomenthyldiphenylphosphine.

When the ligand used is optically active, the dihydropolyprenylcarboxylic acid (I-5) can be prepared in an optically active form.

The hydrogenation catalyst is used in an amount of 0.0001–0.5 mole equivalent, preferably 0.001–0.1 mole equivalent, based on the polyprenylcarboxylic acid (I-4).

Suitable solvents for the hydrogenation reaction are an alcohol, such as methanol or ethanol, distilled after heating with magnesium or treatment with hydrogen in the presence of Raney nickel, and a hydrocarbon, such as benzene or toluene, distilled in the presence of sodium and benzophenone. The amount of the solvent is not critical but suitably the solvent is used in an amount of 5–100 parts by weight, preferably 10–50 parts by weight, per part by weight of the polyprenylcarboxylic acid (I-4).

The hydrogen pressure, reaction temperature and reaction time to be employed in the hydrogenation reaction depend on the apparatus used but generally and preferably are 1–30 atmospheres, 10° C.–60° C. and 6–72 hours, respectively.

It is preferable to perform the hydrogenation reaction in the co-presence of a basic compound, such as sodium methoxide or triethylamine, in an amount of 0.01–0.5 mole equivalent based on the polyprenylcarboxylic acid (I-4) since the hydrogenation reaction is much accelerated thereby.

After the hydrogenation reaction, the reaction mixture is made acidic by adding diluted hydrochloric acid or diluted sulfuric acid and then extracted with a solvent such as hexane, pentane, benzene or diethyl ether, and the solvent is distilled off from the extract to give the dihydropolyprenylcarboxylic acid (I-5).

In the Birch reduction of polyprenylcarboxylic acid (I-4), which is an alternative method, the reaction can be carried out by adding the polyprenylcarboxylic acid (I-4) to liquid ammonia containing lithium dissolved therein. The amount of lithium is 1–100 equivalents, preferably 2–10 equivalents, based on the polyprenylcarboxylic acid (I-4). The amount of liquid ammonia is not critical but suitably is 5–100 parts by weight, preferably 10–50 parts by weight, per part by weight of the polyprenylcarboxylic acid (I-4). Preferably, the polyprenylcarboxylic acid (I-4) is added in the form of a solution in anhydrous diethyl ether or anhydrous tetrahydrofuran, since this method is convenient and moreover improves the homogeneity of the reaction mixture.

This Birch reduction is preferably performed at the boiling point of liquid ammonia (about −33° C.). However, it is also possible to perform the reaction, as necessary, at a lower temperature, or at a higher temperature than the boiling point in a pressure-resistant vessel under pressure. After stirring at a temperature such as mentioned above for about 0.5–10 hours, ammonium chloride, for instance, is added to the reaction mixture for decomposing the excess lithium and then the ammonia is distilled off to give the dihydropolyprenylcarboxylic acid (I-5) in a crude form.

The dihydropolyprenylcarboxylic acid (I-5) can be purified by any of the isolation/purification techniques so far known in the art. Chromatography is especially preferred because of simplicity and convenience.

The esterification of the dihydropolyprenylcarboxylic acid (I-5) to the dihydropolyprenylcarboxylate of formula (I-3) can be carried out in the manner so far known for the esterification of higher fatty acids. Thus, for example, the esterification can be performed by dissolving the above dihydropolyprenylcarboxylic acid (I-5) in a lower alcohol into which dried hydrogen chloride gas has been injected and stirring the mixture at room temperature or at a temperature up to the boiling point of the solvent. For synthesizing the methyl ester of dihydropolyprenylcarboxylic acid (I-5), the methylation can also be carried out by dissolving the above dihydropolyprenylcarboxylic acid (I-5) in a solvent such as anhydrous diethyl ether or anhydrous tetrahydrofuran and then adding thereto a solution of diazomethane in diethyl ether and allowing the reaction to proceed. The lower alkyl esters of dihydropolyprenylcarboxylic acid (I-5) can be purified by practically the same method as mentioned above for the purification of dihydropolyprenylcarboxylic acid (I-5) itself.

Reduction of the dihydropolyprenylcarboxylic acid (I-5) or the ester thereof represented by formula (I-3) with lithium aluminum hydride, for instance, gives dolichol.

The compound of formula (I-6) [hereinafter referred to as "polyprenylnitrile (I-6)"] can be produced by subjecting the polyprenylacetone (I-1) to the Wittig reaction with a dialkylphosphonoacetonitrile (Wittig reagent) of the formula

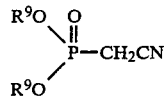

(VII)

wherein $R^9$ is a lower alkyl group, such as

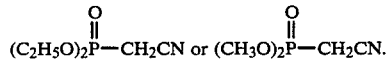

This Wittig reaction can be carried out in the same manner as mentioned for the Wittig reaction between polyprenylacetone (I-1) and a compound of formula (VI), using the same solvent, same basic compound, same reaction conditions (temperature, proportions of reactants, etc.) and same procedure. After completion of the Wittig reaction, the reaction mixture is poured into water and the organic substance is extracted, whereupon the desired polyprenylnitrile (I-6) can be obtained in a crude form.

The polyprenylnitrile (I-6) can be purified by any of the isolation/purification techniques per se known so far. Chromatography is especially preferred because of simplicity and convenience. The thus-obtained polyprenylnitrile can be converted to the polyprenylcarboxylic acid (I-4) directly or via the amide of formula (I-10). Dolichol can be derived from the polyprenylcarboxylic acid (I-4) by the selective hydrogenation and reduction.

The hydrolysis of polyprenylnitrile (I-6) to the amide of formula (I-10) is carried out by vigorously stirring the polyprenylnitrile (I-6) with activated manganese dioxide in a halogenated hydrocarbon solvent such as methylene chloride or chloroform. The solvent is used in an amount of 2–200 parts by weight, preferably 5–50 parts by weight, per part by weight of the polyprenylnitrile (I-6). Activated manganese dioxide is used in an amount of 2–100 parts by weight, preferably 5–20 parts by weight, per part by weight of the polyprenylnitrile (I-6). The reaction temperature may be in the range of 0° C. to the boiling point of the solvent but room temperature is employed in most cases. The reaction time is about 10–120 hours in case the reaction is carried out at room temperature, although it may vary depending on the reaction temperature. After completion of the reaction, the manganese dioxide is filtered off and the organic layer is concentrated to give the amide of formula (I-10). The amide of formula (I-10) can be purified conveniently by chromatography.

The following schematic representation will serve for better understanding of the foregoing description.

Scheme 1

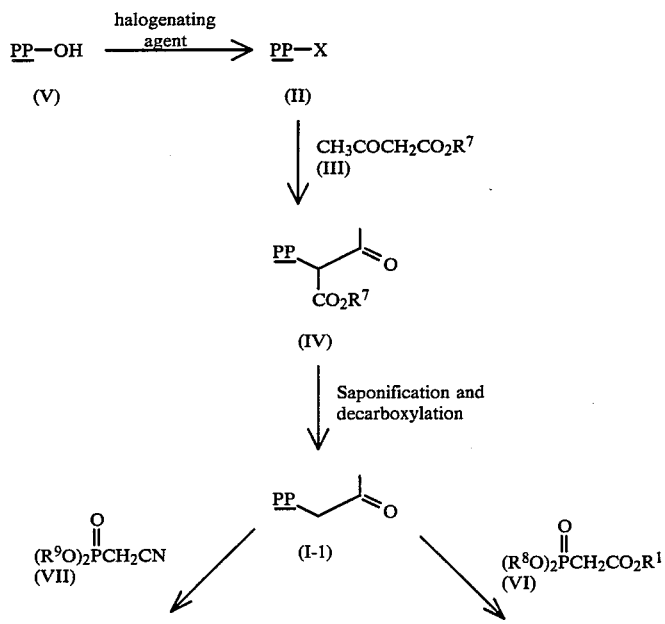

-continued
Scheme 1

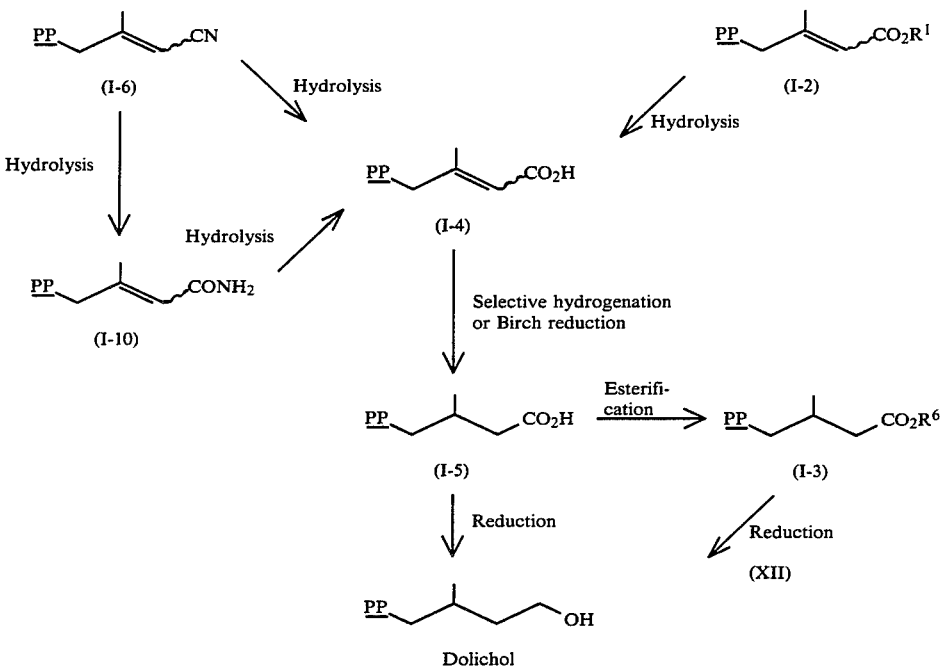

In the above schematic representation and also in the description which follows, PP represents a group of the formula

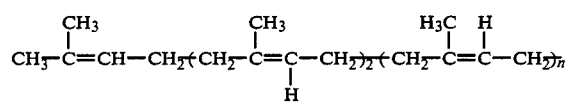

wherein

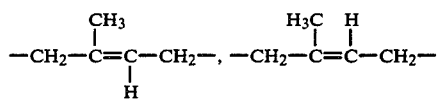

and n are as defined above.

The compound of formula (I-8) can be produced by reacting the polyprenylacetone (I-1) with a lower alkyl cyanoacetate in the presence of a base and/or an acid.

Suitable examples of the lower alkyl cyanoacetate are

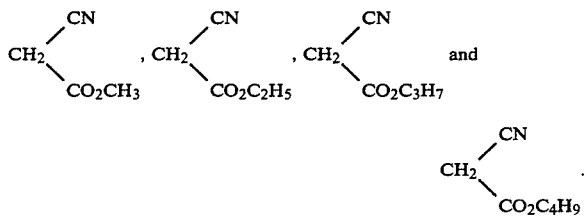

The cyanoacetic acid ester is used in an amount of 0.5–10.0 mole equivalents, preferably 0.7–1.5 mole equivalents, more preferably 0.8–1.0 mole equivalent, based on the polyprenylacetone (I-1).

The reaction of the polyprenylacetone (I-1) and the lower alkyl cyanoacetate is desirably carried out in a solvent inert to the reaction. Suitable examples of the solvent are hexane, heptane, benzene, toluene, xylene and chloroform. The amount of the solvent is not critical but generally the solvent is used in an amount of 5–200 parts by weight, preferably 10–100 parts by weight, per part by weight of the polyprenylacetone (I-1).

The presence of a base and/or an acid is essential for the reaction of the polyprenylacetone (I-1) with the lower alkyl cyanoacetate. Suitable examples of the base and/or acid are ammonium acetate-acetic acid, acetamide-acetic acid, pyridine-acetic acid, piperidine, and $\epsilon$-amino-n-caproic acid. The above base and/or acid is used in an amount of 0.1–10.0 mole equivalents, preferably 0.1–1.0 mole equivalent, based on the polyprenylacetone (I-1).

The desired reaction can be carried out by dissolving the polyprenylacetone (I-1), the cyanoacetic acid ester and the above base and/or acid in the above solvent and stirring the mixture under heating conditions. For the completion of the reaction, it is preferable to remove the by-product water. A convenient method of removing water consists in distilling off the water azeotropically with the solvent. It is therefore preferable to select the boiling point of the abovementioned solvent as the reaction temperature and, under such reaction conditions, the desired reaction can be driven to completion by conducting the reaction for 1–24 hours, preferably 2–10 hours. After completion of the reaction, the solvent is distilled off to give the compound of formula (I-8) in a crude form.

The compound of formula (I-8) can be purified by any of the so far known isolation/purification techniques. Among them, chromatography is especially preferable because of simplicity and convenience.

Selective reduction of the compound of formula (I-8) can give the compound of formula (I-9). The reducing agent for this purpose may be a mild one, such as sodium borohydride, lithium borohydride or sodium cyanoborohydride, and sodium borohydride is the most preferable. The reducing agent is generally used in an amount of 0.5–10 equivalents, preferably 1–5 equivalents, based on the compound of formula (I-8), although the amount depends on the kind of reducing agent.

This reduction is carried out in an appropriate solvent. Suitable examples of the solvent are ethanol and isopropanol.

In most cases, the reduction can proceed at room temperature. If necessary, however, other temperature than room temperature can be selected within the range of $-20°$ C. to $+80°$ C. Stirring under such temperature conditions for about 5 minutes to about 10 hours can drive the reaction to completion.

After completion of the reaction, the compound of formula (I-9) can be conveniently purified by chromatography as in the case of the compound of formula (I-8).

Hydrolysis and decarboxylation of the thus-obtained compound of formula (I-9) gives the compound of formula (I-7).

The hydrolysis of the compound of formula (I-9) can be carried out by a method similar to that so-far used in hydrolyzing higher fatty acid esters. Thus, for instance, the reaction can be performed by stirring the compound of formula (I-9) with sodium hydroxide or potassium hydroxide in an alcohol solvent such as methanol, ethanol, isopropanol, ethylene glycol or propylene glycol.

the temperature conditions employed but in most cases is within the range of about 0.5–24 hours.

After carrying out the hydrolysis reaction in the above manner, the reaction mixture, preferably under room temperature or ice cooling conditions, is made acidic with a mineral acid such as hydrochloric acid or sulfuric acid to a pH value of about 1–4 and then extracted with hexane, benzene, diethyl ether or ethyl acetate, for instance, and the solvent is distilled off to give a carboxylic acid which is represented by formula (I-9) when $R^2$ in said formula is a hydrogen atom. The decarboxylation of said carboxylic acid is preferably carried out by dissolving the same in 5–100 parts by weight, per part by weight of the carboxylic acid, of pyridine and refluxing the mixture in the presence of 0.01–1.0 parts by weight of copper dust for 1–5 hours. Removal of the copper dust by filtration, concentration of the filtrate, dissolution of the concentrate in a solvent such as hexane or diethyl ether, washing and drying of the solution and removal of the solvent by distillation give the compound of formula (I-7) in a crude form. This compound can be conveniently purified by chromatography. The thus-obtained compound of formula (I-7) can be converted to the corresponding dihydropolyprenylcarboxylic acid (I-5) by hydrolysis either directly or via the amide of formula (I-11). Dolichol can be derived from the dihydropolyprenylcarboxylic acid (I-5) by the reduction.

The above-mentioned processes for the synthesis of the compounds of formulas (I-6), (I-7) and (I-8) from the polyprenylacetone (I-1) and of dolichol via said compounds can be represented schematically as follows:

Scheme 2

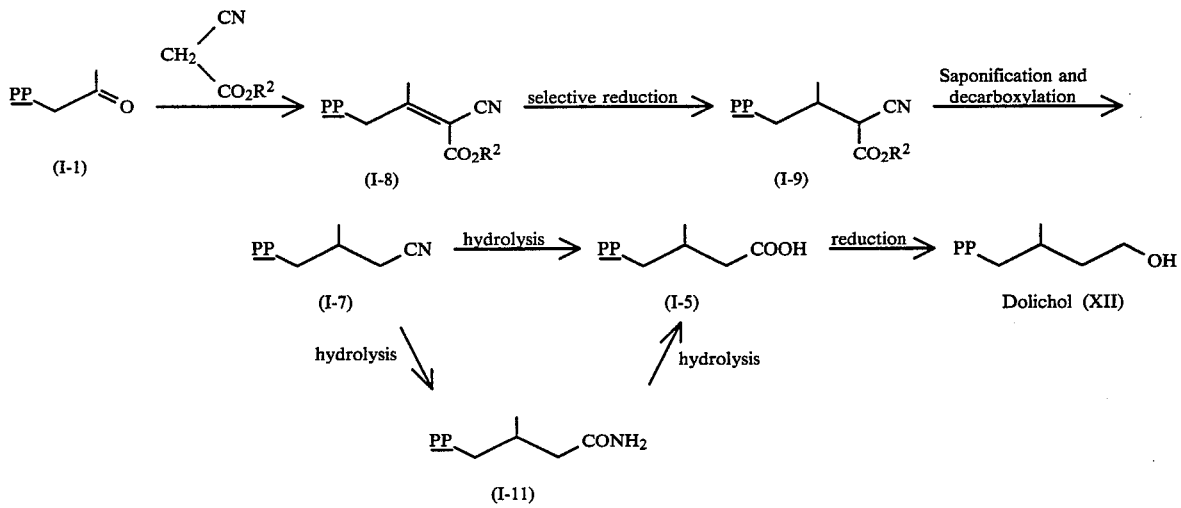

Sodium hydroxide or potassium hydroxide is desirably used in an amount of about 1.0–20.0 mole equivalents, preferably 1.5–10.0 mole equivalents, based on the compound of formula (I-9). An alcohol such as mentioned above is suitable as the reaction solvent and it is also preferable to add a small amount of a hydrocarbon solvent such as hexane, pentane, benzene or toluene for increasing the solubility of the compound of formula (I-9). For enabling smooth progress of the above-mentioned hydrolysis while preventing hydrolysis of the cyano group, it is desirable to maintain the reaction temperature within the range of 0° C. to 30° C. The time required for the completion of the reaction depends on The compound of formula (I-12) can be produced by subjecting the polyprenylacetone (I-1) to the Wittig reaction with a compound of the formula

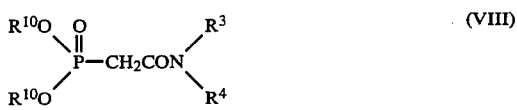

wherein $R^{10}$ is a lower alkyl group, and $R^3$ and $R^4$ are as defined above for formula (I-12). This Wittig reaction can be carried out in the same manner as mentioned above for the Wittig reaction between the polyprenylacetone (I-1) and the compound of formula (VI), using the same solvent, same basic compound, same reaction conditions (temperature, proportions of reactants, etc.) and same procedure as mentioned above. The following are examples of the Wittig reagent of formula (VIII) which are especially suited for use:

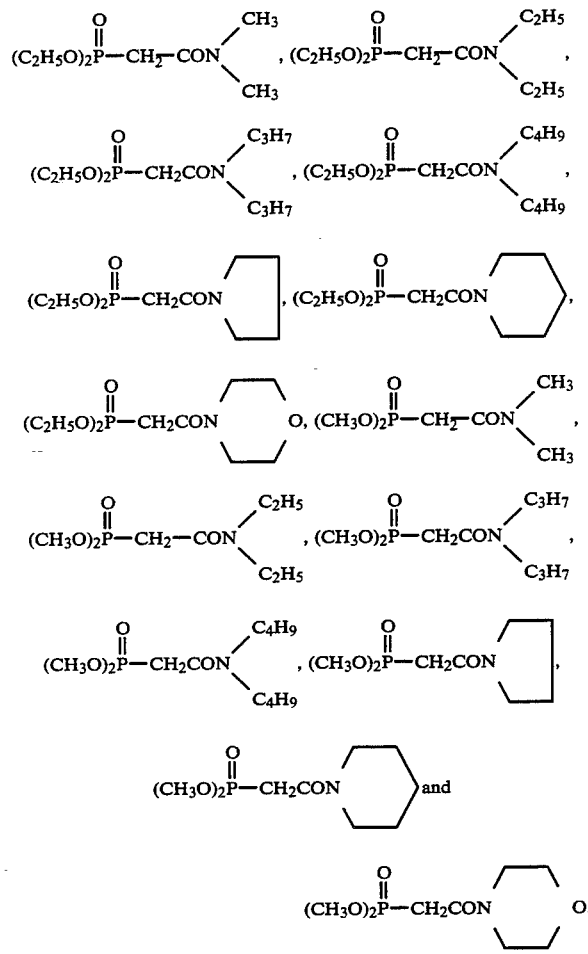

The compound of formula (I-12) can also be produced by reacting the polyprenylcarboxylic acid (I-4) or a reactive derivative thereof, for instance an acid halide or an acid anhydride, with an amine of the formula

 (IX)

wherein $R^3$ and $R^4$ are as defined above for formula (I-12).

Similarly, the compound of formula (I-13) can be produced by reacting the polyprenylcarboxylic acid (I-4) or a reactive derivative thereof, for instance an acid halide or an acid anhydride, with an amine of the formula $H_2N-R^5$ (X)

wherein $R^5$ is as defined above for formula (I-13).

The amidation of the polyprenylcarboxylic acid (I-4) with the amine of formula (IX) or (X) can be generally carried out by any of the known methods. Thus, for example, the amidation can be conducted using a dehydration-condensation agent such as N,N'-dicyclohexylcarbodiimide, N,N'-diethylcarbodiimide, trialkyl phosphite or pohsphorus oxychloride, and the use of N,N'-dicyclohexylcarbodiimide, is convenient. This reaction is desirably carried out in a solvent. Suitable solvents are halogenated hydrocarbons such as methylene chloride and chloroform. The amount of the solvent is not critical. Generally, however, the solvent is used in an amount of 2–100 parts by weight, preferably 5–50 parts by weight, per part by weight of the polyprenylcarboxylic acid (I-4). The use of a well-dried solvent is preferable for the desired reaction. N,N'-Dicyclohexylcarbodiimide and the amine of formula (IX) or (X) each is used in an amount of about 1 mole equivalent in relation to the polyprenylcarboxylic acid (I-4), which amount is sufficient for the purpose. The reaction temperature is preferably within the range of from −20° C. to the boiling point of the solvent, more preferably within the range of from 0° C. to room temperature. Generally, a reaction time of 1–2 hours is sufficient, although the time required may vary depending on the temperature conditions employed. In a preferred embodiment, N,N'-dicyclohexylcarbodiimide is added gradually to a solution of the polyprenylcarboxylic acid (I-4) in methylene chloride with ice cooling and, after stirring for 15–30 minutes, the amine of formula (IX) or (X) is added gradually, and then the resulting mixture is warmed gradually to room temperature. The floating solid is filtered off, the filtrate is poured into cold water, the organic layer is separated, washed in sequence with diluted hydrochloric acid, water, saturated aqueous sodium bicarbonate solution and saturated aqueous sodium chloride solution and then dried, and the solvent is distilled off to give the polyprenylcarboxylic acid amide of formula (I-12) or (I-13) in a crude form, which can be conveniently purified by chromatography.

Reduction of the amide of formula (I-12) gives the amine of formula (I-14) and, similarly, reduction of the amide of formula (I-13) gives the amine of formula (I-15). Suitable reducing agents in the reduction of said amides are complex metal hydrides such as lithium aluminum hydride, sodium aluminum hydride, sodium borohydride and lithium borohydride. The reducing agent is generally used in an amount of 0.5–10 equivalents, preferably 1–5 equivalents, based on the amide of formula (I-12) or (I-13), although the amount may vary depending on the kind of reducing agent.

The reduction is carried out in an appropriate solvent. When lithium aluminum hydride is used as the reducing agent, ether solvents such as diethyl ether and tetrahydrofuran can be used among others. When sodium borohydride is used, alcohol solvents such as ethanol and isopropanol as well as pyridine can be used among others.

Generally, the reduction is preferably carried out at a temperature in the vicinity of the boiling point of the solvent. Stirring at such a temperature for about 2–20 hours can complete the reaction.

The isolation and purification of the amine of formula (I-14) or (I-15) can be generally carried out by any of the conventional isolation/purification methods, among which chromatography is convenient. The adsorbent to be used in chromatography includes among others silica gel, alumina, activated carbon and cellulose, among which silica gel and alumina are preferred. A preferable developing solvent is a mixture of a hydrocarbon solvent, such as hexane, pentane, petroleum ether or benzene, and a small amount of a polar solvent, such as diethyl ether, diisopropyl ether, chloroform, ethyl acetate, ethanol or n-butylamine.

The compound of formula (I-16) can be produced by isomerization of the compound of formula (I-14) as a result of hydrogen shift. Similarly, isomerization of the compound of formula (I-15) gives the compound of formula (I-17). The isomerization of the compound of formula (I-14) to the compound of formula (I-16) or of the compound of formula (I-15) to the compound of formula (I-17), which involves hydrogen shift, can be carried out by using, for example, the rhodium(I) complex catalyst. The catalyst is used in an amount of 0.0001-1 mole equivalent, preferably 0.001-0.1 mole equivalent, more preferably 0.005-0.05 mole equivalent, based on the amine of formula (I-14) or (I-15). This reaction is desirably performed in a solvent under an inert gas atmosphere, such as argon or nitrogen. Examples of the solvent are ethers such as diethyl ether, tetrahydrofuran and 1,2-dimethoxyethane, among which the use of tetrahydrofuran is preferred. The amount of the solvent is not critical. Generally, however, the solvent is used in an amount of 2-200 parts by weight, preferably 5-50 parts by weight, per part by weight of the amine of formula (I-14) or (I-15). The reaction temperature may be selected in the range of from 20° C. to the boiling point of the solvent, but is preferably 40° C.-60° C. It is desirable to perform the reaction at the last-mentioned temperature for about 12-24 hours. When the rhodium complex (I) contains an optically active diphosphine ligand such as (R)-(+)-2,2'-bis(diphenylphosphino)-1,1'-binaphthyl (hereinafter abbreviated as "R-BINAP") and is, for example, [Rh(R-BINAP)(1,5-cyclooctadiene)]ClO$_4$, asymmetric hydrogen shift takes place, whereby the compound of formula (I-16) or (I-17) can be obtained in an optically active form.

The compound of formula (I-16) and the compound of formula (I-17) each can be converted to dolichol by hydrolysis to the corresponding aldehyde followed by reduction with sodium borohydride, for instance.

The synthesis of the compounds of formulas (I-12), (I-13), (I-14), (I-15), (I-16) and (I-17) and the conversion to dolichol, which have been described above, can be represented schematically as follows:

Scheme 3

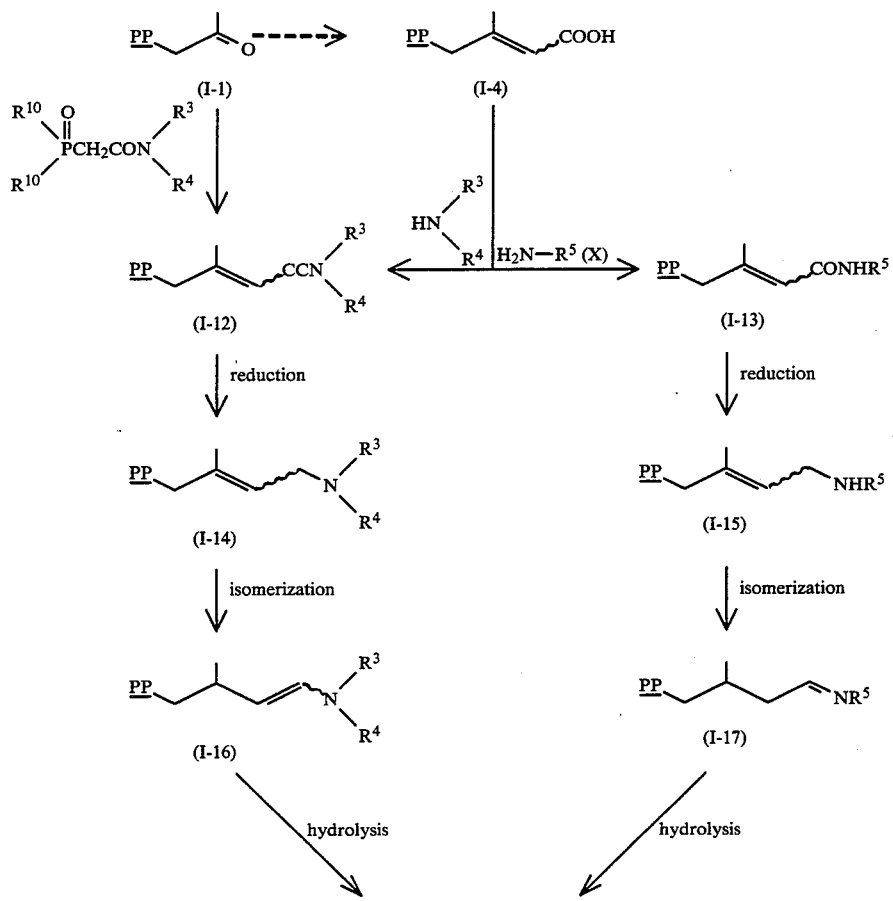

Scheme 3

-continued

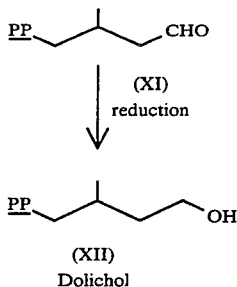

(XI)

↓ reduction

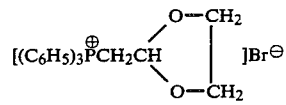

(XII)
Dolichol

The compound of formula (I-18) can be produced by subjecting the polyprenylacetone (I-1) to the Wittig reaction with 1,3-dioxan-2-ylmethyltriphenylphosphonium bromide of the formula $$[(C_6H_5)_3\overset{\oplus}{P}CH_2CH\begin{matrix}O-CH_2\\ \\O-CH_2\end{matrix}]Br^{\ominus}$$

followed by removal of the —CHO protecting group in the product. This Wittig reaction is required to be carried out in a solvent inert to the reaction. Suitable examples of the solvent are dimethylformamide, tetrahydrofuran, diethyl ether and benzene. For the desired reaction, it is preferred that the solvent to be used is in a well-dried, anhydrous state. From the same viewpoint, the reaction system is preferably substituted with an inert gas such as nitrogen or argon. The solvent is preferably used in an amount of 5-50 parts by weight, preferably 10-30 parts by weight, per part by weight of the polyprenylacetone (I-1) to be subjected to the reaction.

The reaction using the above Wittig reagent which contains an oxygen atom beta to the phosphorus atom is preferably carried out by adding a base dropwise to a mixture of the Wittig reagent and the polyprenylacetone (I-1) so that the phosphoylide can react with the polyprenylacetone (I-1) as soon as it is formed from the Wittig reagent and the base and so that the elimination reaction, which is a side reaction, can be reduced to the minimum. Preferred examples of the base which is to be used in this reaction are n-butyllithium, methyllithium, phenyllithium, lithium hydride, potassium hydride, lithium methoxide, sodium methoxide, sodium ethoxide and sodium amide. The base selected from among these is added dropwise to said mixture in an amount of about 0.5-1.5 mole equivalents based on the Wittig reagent. During the addition, the bath temperature is maintained at −30° C. to +120° C., preferably at 20° C. to 100° C., and after the dropwise addition, stirring is continued at a temperature within the above-mentioned range for about 0.5-5 hours so as to complete the reaction. The Wittig reagent is desirably used in an amount of 0.5-10.0 mole equivalents, preferably 0.8-8.0 mole equivalents, more preferably 1.0-5.0 mole equivalents, based on the polyprenylacetone (I-1). After completion of the Wittig reaction, the —CHO protecting group is removed by treatment with a mineral acid such as hydrochloric acid or sulfuric acid to give the compound of formula (I-18).

Furthermore, direct oxidation of the polyprenol of formula (V) in which n is 12-19 can give the compound of formula (I-18) in which n is 11-18.

The oxidizing agent to be used for said oxidation may be the one generally used in the oxidation of an allyl alcohol to an α,β-unsaturated aldehyde and thus includes, for example, manganese dioxide, chromic anhydride-pyridine, pyridinium chlorochromate (PCC) and pyridinium dichromate (PDC), among which manganese dioxide is especially preferable. The oxidizing agent is used in an amount of 1-200 moles, preferably 2-100 moles, per mole of the polyprenol of formula (V). This oxidation is preferably carried out in a solvent. A preferred example of the solvent is methylene chloride. When manganese dioxide is used as the oxidizing agent, halogenated hydrocarbons such as chloroform and carbon tetrachloride, hydrocarbons such as petroleum ether, hexane, pentane and benzene, ketones such as acetone and methyl ethyl ketone, and ethers such as diethyl ether and diisopropyl ether may also be preferably used. Although the amount of the above solvent is not critical, the solvent is generally used in an amount of 1-200 parts by weight, preferably 2-100 parts by weight, more preferably 5-500 parts by weight, per part by weight of the polyprenol of formula (V). The oxidation reaction temperature is desirably within the range of −30° C. to +100° C., preferably −10° C. to +60° C. For the smooth completion of the reaction, it is required to stir the reaction mixture at the above temperature, preferably for about 0.5-48 hours. The progress of the reaction can be conveniently and preferably confirmed by tracing the decrease of the starting polyprenol of formula (V) by thin layer chromatography. After completion of the reaction, the reaction mixture is filtered and the solvent is distilled off from the filtrate to give the compound of formula (I-18). This compound, too, can be conveniently purified by chromatography.

The thus-obtained aldehyde of formula (I-18) can be converted to dolichol, for example, by selective reduction of the α,β-unsaturated bond followed by further reduction of the —CHO group to a —CH₂OH group.

The above-mentioned methods of producing the compounds of formula (I) according to the present invention are respectively applicable not only to individual polyprenyl compounds with the definite number of cis-isoprene units but also to polyprenyl homolog mixtures with a distribution with respect to the number of cis-isoprene units. Therefore, the compounds of the present invention each can be obtained either in the form of a single individual compound or in the form of a homolog mixture showing substantially the same ho- TABLE 2-continued

| | | | | | |
|---|---|---|---|---|---|
| 15 | 135.15 | 125.12 | 58.99 | 39.78 | 32.29 | 32.05 |
| 16 | 135.15 | 125.11 | 58.98 | 39.77 | 32.28 | 32.05 |
| 17 | 135.15 | 125.12 | 59.00 | 39.77 | 32.29 | 32.05 |
| 18 | 135.16 | 125.10 | 58.98 | 39.77 | 32.29 | 32.05 |
| 19 | 135.15 | 125.10 | 58.98 | 39.78 | 32.28 | 32.05 |

$^{13}C$—NMR δ (ppm)

| $\underline{n}$ (number of cis-isoprene units) | CH$_3$ \ /  \ $\underline{C}$H$_2$— | CH$_3$ \ / H \ $\underline{C}$H$_2$ | CH$_3$ \ / \ $\underline{C}$H$_3$   H | $\underline{C}$H$_3$ \ / \ CH$_3$   H | $\underline{C}$H$_3$ \ / \     H |
|---|---|---|---|---|---|
| 11 | 26.47 | 23.42 | 25.67 | 17.64 | 15.98 |
| 12 | 26.47 | 23.42 | 25.66 | 17.64 | 15.98 |
| 13 | 26.48 | 23.42 | 25.67 | 17.65 | 15.99 |
| 14 | 26.47 | 23.42 | 25.66 | 17.64 | 15.97 |
| 15 | 26.49 | 23.42 | 25.65 | 17.65 | 15.99 |
| 16 | 26.49 | 23.42 | 25.65 | 17.64 | 15.98 |
| 17 | 26.49 | 23.41 | 25.66 | 17.65 | 15.99 |
| 18 | 26.48 | 23.41 | 25.64 | 17.64 | 15.99 |
| 19 | 26.49 | 23.42 | 25.65 | 17.65 | 15.98 |

REFERENCE EXAMPLE 2

Synthesis of polyprenyl bromide 12.4 g of polyprenol of formula (V) in which n=15 and 1 ml of pyridine were added to 200 ml of n-hexane. To the resulting solution was added dropwise 2.0 g of phosphorus tribromide at room temperature (about 20° C.) under an atmosphere of nitrogen. After the addition, the mixture was stirred overnight at room temperature under an atmosphere of nitrogen. The n-hexane solution was transferred to a separating funnel, washed three times with about 50 ml of water and then dried over anhydrous magnesium sulfate. The n-hexane was distilled off to give 12.0 g of a slightly yellow liquid product. When this product was analyzed by NMR spectroscopy, the signal (doublet, δ=4.08) assignable to the —CH$_2$OH group of the starting polyprenol had disappeared, and a signal (doublet, δ=3.91) assignable to —CH$_2$Br had appeared newly. FD-MASS analysis of this liquid product gave m/e=1304. Based on these analytical data, the above product was identified to be polyprenyl bromide of formula (II) in which n=15 and X=Br.

By a procedure similar to that described above, polyprenyl bromide species in which n was other than 15 and polyprenyl bromide mixtures having various compositions with n being distributed in the range of 11-19 were synthesized.

REFERENCE EXAMPLE 3

Synthesis of polyprenyl chloride 12.4 g of polyprenol of formula (V) in which n=15 and 1.0 ml of pyridine were added to 200 ml of n-hexane. To the resulting solution was added dropwise 1.5 g of thionyl chloride at room temperature under an atmosphere of nitrogen. After the addition, the mixture was further stirred at room temperature for 2 hours. The reaction mixture was then worked up in the same way as in Reference Example 2 to give 11.2 g of a pale yellow liquid. IR analysis of the resulting liquid showed that the absorption attributable to the —OH group of the starting polyprenol had disappeared. NMR analysis showed that the signal assignable to —CH$_2$OH of the starting polyprenol had disappeared, and a signal (doublet, δ=3.95) assignable to —CH$_2$Cl had newly appeared. FD-MASS analysis gave m/e=1260. From these analytical data, the above product was identified to be polyprenyl chloride of formula (II) in which n=15 and X=Cl.

By a procedure similar to that described above, polyprenyl chloride species in which n was other than 15 and polyprenyl chloride mixtures having various compositions with n being distributed in the range of 11-19 were synthesized.

EXAMPLE 1

Synthesis of polyprenylacetone

A three-necked flask was charged with 30 ml of anhydrous tetrahydrofuran and 640 mg of 50% sodium hydride and thereto was added dropwise 1.57 g of ethyl acetoacetate with stirring at room temperature. After the vigorous hydrogen gas evolution subsided, the flask inside was substituted with nitrogen, and the temperature of the reaction system was raised gradually, and then stirring was continued under reflux for an hour. Thereafter, the reaction system was cooled to room temperature, and thereto was added dropwise a solution of 4.30 g of polyprenyl bromide of formula (II) in which n=15 and X=Br as synthesized by the procedure of Reference Example 2 in 10 ml of tetrahydrofuran. The mixture was stirred overnight at room temperature. The solvent was distilled off from the reaction mixture using a rotary evaporator, the residue was poured into about 20 ml of water and extracted with diethyl ether, the diethyl ether layer obtained was washed in sequence with water, diluted hydrochloric acid, water and aqueous sodium bicarbonate solution, and dried over anhydrous magnesium sulfate, and the diethyl ether was distilled off using a rotary evaporator to give a yellow oil. This oil was heated at 150° C. under vacuum (1 mmHg) for 30 minutes for distilling off low-boiling components. The residue was purified by silica gel column chromatography [developing solvent: hexane-ethyl acetate=98:2 (by volume)] to give 2.48 g of a pale yellow oil. The analytical data for this oil are shown below.

IR analysis: 1740, 1715, 1660, 830 cm$^{-1}$.

$^1$H-NMR analysis: $\delta_{CCl_4}^{ppm}$ 1.21(3H, t, —CO$_2$CH$_2$C$\underline{H}_3$), 3.21 molog distribution pattern as that in a natural dolichol, for instance.

The following examples and reference examples will illustrate the invention in more detail. In the examples and reference examples, the IR analysis was performed by the liquid film method, and the NMR analysis was carried out using TMS (tetramethylsilane) as the internal standard. The m/e values shown for the field desorption mass spectrometry (FD-MASS analysis) are corrected on the $^1$H, $^{12}$C, $^{14}$N, $^{16}$O and $^{79}$Br basis.

REFERENCE EXAMPLE

Isolation of polyprenol

Ten kilograms (in the undried state) of leaves of *Ginkgo biloba*, which were collected in Kurashiki City, Japan at the end of October, were dried with hot air at about 40° C. for 24 hours, and then extracted with 80 liters of chloroform at about 15° C. for 7 days. The chloroform was removed from the extract and 5 liters of petroleum ether was added to the concentrate. The insoluble matter was separated by filtration. The filtrate was concentrated and chromatographed on a silica gel column using chloroform as an eluant to separate a fraction having an Rf value of 0.50 and 0.19 as determined by silica gel thin-layer chromatography (Merck TLC plate silica gel 60F$_{254}$ precoated, layer thickness, 0.25 mm; developed by 10 cm) using a mixed solvent of n-hexane-ethyl acetate (9:1 by volume) as a developing solvent. There was obtained about 37 g of an oily product. In the above thin-layer chromatography, solanesyl acetate had an Rf value of 0.41. About 400 ml of acetone was added to the oily product to dissolve acetone-soluble components. The insoluble matter was filtered off, and the filtrate was concentrated. The oily product obtained was heated at 65° C. for 2 hours together with 400 ml of methanol, 40 ml of water and 20 g of sodium hydroxide. The methanol was then distilled off and diethyl ether (500 ml) was added to the residue to perform extraction. The etheral layer was washed five times with about 100 ml of water and dried over anhydrous sodium sulfate. The solvent was distilled off to give 24.2 g of an oily product.

The oily product was then chromatographed on a column of about 1 kg of silica gel using a mixture of n-hexane/isopropyl ether (90/10 by volume) as an eluent to separate a fraction having an Rf value of 0.19 as determined by the same thin-layer chromatography as described above, whereby 21.8 g of an oily product was obtained. The oily product was a polyprenol fraction having a purity of more than 95%. This was analyzed by a high-performance liquid chromatography using a Merck semipreparative chromatography column Li-Chrosorb RP18-10 (C$_{18}$ type), a mixed solvent of acetone-methanol (90:10 by volume) as the developing solvent, and a differential refractometer as the detector. The area proportions of the individual peaks on the resulting chromatogram were determined, and the following results were obtained.

| Peak No. | Number of cis-isoprene units (n) | Area proportion (%) |
|---|---|---|
| 1 | 11 | 0.3 |
| 2 | 12 | 1.1 |
| 3 | 13 | 5.9 |
| 4 | 14 | 25.6 |
| 5 | 15 | 39.4 |
| 6 | 16 | 19.2 |
| 7 | 17 | 5.9 |
| 8 | 18 | 1.8 |
| 9 | 19 | 0.8 |

The individual components were separated from the above oily product (containing more than 95% of polyprenols) by using the same high-performance liquid chromatography column as mentioned above. By mass spectroscopy, infrared absorption spectroscopy, $^1$H-NMR spectroscopy and $^{13}$C-NMR spectroscopy, these compounds were determined to be polyprenols having the structure represented by the formula (V).

The results of FD-MASS of these components and their δ values in $^1$H-NMR spectra are summarized in Table 1. The δ values of these components in $^{13}$C-NMR spectra are summarized in Table 2.

In the $^1$H-NMR data, (b) represents a broad signal, (d), a doublet signal, and (t), a triplet signal.

TABLE 1

| n (number of cis-isoprene units) | FD-MASS (m/e) Found | FD-MASS (m/e) Calcd. | $^1$H—NMR δ (ppm) =CHCH$_2$OH | =CH— | —CH$_2$OH | —CH$_2$— | H$_3$C\_/H —CH$_2$ CH$_2$OH | H$_3$C\_/H —CH$_2$ .CH$_2$— | H$_3$C\_/CH$_2$— —CH$_2$ H |
|---|---|---|---|---|---|---|---|---|---|
| 11 | 970 | 970 | 5.44 (t) | 5.11 (b) | 4.08 (d) | 2.04 (b) | 1.74 | 1.68 | 1.60 |
| 12 | 1038 | 1038 | 5.44 (t) | 5.12 (b) | 4.08 (d) | 2.04 (b) | 1.74 | 1.68 | 1.60 |
| 13 | 1106 | 1106 | 5.43 (t) | 5.12 (b) | 4.08 (d) | 2.04 (b) | 1.74 | 1.68 | 1.60 |
| 14 | 1174 | 1174 | 5.44 (t) | 5.12 (b) | 4.08 (d) | 2.04 (b) | 1.74 | 1.68 | 1.60 |
| 15 | 1242 | 1242 | 5.44 (t) | 5.13 (b) | 4.08 (d) | 2.04 (b) | 1.74 | 1.68 | 1.60 |
| 16 | 1310 | 1310 | 5.44 (t) | 5.14 (b) | 4.08 (d) | 2.04 (b) | 1.74 | 1.68 | 1.60 |
| 17 | 1378 | 1378 | 5.44 (t) | 5.13 (b) | 4.08 (d) | 2.04 (b) | 1.74 | 1.68 | 1.60 |
| 18 | 1446 | 1446 | 5.43 (t) | 5.13 (b) | 4.08 (d) | 2.05 (b) | 1.74 | 1.68 | 1.60 |
| 19 | 1514 | 1514 | 5.44 (t) | 5.13 (b) | 4.08 (d) | 2.04 (b) | 1.74 | 1.68 | 1.60 |

TABLE 2

| n (number of cis-isoprene units) | $^{13}$C—NMR δ (ppm) \C— / | =CH— | —CH$_2$OH | CH$_3$ \_/ \_CH$_2$ | CH$_3$ \_/ —CH$_2$ | CH$_3$ \_/CH$_3$ —CH$_2$ | CH$_3$ \_/ —CH$_2$ | CH$_3$ \_/CH$_3$ —CH$_2$ |
|---|---|---|---|---|---|---|---|---|
| 11 | 135.17 | 125.09 | 59.00 | 39.77 | 32.27 | | 32.04 | |
| 12 | 135.17 | 125.10 | 58.99 | 39.78 | 32.28 | | 32.05 | |
| 13 | 135.16 | 125.08 | 58.99 | 39.78 | 32.27 | | 32.05 | |
| 14 | 135.17 | 125.09 | 59.00 | 39.77 | 32.27 | | 32.04 | |

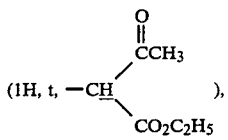

4.11(2H, q, —CO$_2$CH$_2$CH$_3$).

FD-MASS analysis: m/e=1354.

Based on the above analytical results, the pale yellow oil was identified as ethyl polyprenylketocarboxylate of formula (IV) in which n=15 and R$^7$=C$_2$H$_5$.

This ethyl polyprenylketocarboxylate was added to a solution of 0.5 g of sodium hydroxide in 20 ml of ethanol and 5 ml of water, the mixture was stirred under reflux for 3 hours, most of the ethanol was then distilled off using a rotary evaporator, and the residue was poured into about 20 ml of water. The resulting mixture was made acidic by adding concentrated hydrochloric acid portionwise to pH of about 2 and extracted with hexane. The hexane layer was washed well with saturated aqueous sodium chloride solution and then dried over anhydrous magnesium sulfate, and the solvent was distilled off to give a yellow viscous oil. This oil was purified by silica gel column chromatography [developing solvent: hexane-ethyl acetate=98:2 (by volume)] to give 1.98 g of a pale yellow viscous oil. The analytical data for this oil are shown below.

IR analysis: 1715, 1660, 830 cm$^{-1}$.

$^1$H-NMR analysis: $\delta_{CCl_4}^{ppm}$ 1.53(s, 9H), 1.62(s, 48H), 1.7–2.4(m, 75H), 5.05(br, 18H).

FD-MASS analysis: m/e=1282.

The above analytical results demonstrated that the pale yellow oil was the polyprenylacetone of formula (I-1) in which n=15.

Essentially following the above procedure, species of polyprenylacetone of formula (I-1) in which n=11, 12, 13, 14, 16, 17, 18 and 19 were synthesized from the corresponding species of polyprenyl bromide of formula (II) in which n=11–19 but other than 15 in almost the same yields as in the case of the polyprenylacetone in which n=15. The characteristic absorptions on their infrared absorption spectra and the characteristic signals on their $^1$H-NMR spectra were respectively in agreement with those of the above-mentioned polyprenylacetone in which n=15 with respect to their positions.

The results of FD-MASS analysis for the polyprenylacetone species were as follows:

| The value of n in the starting polyprenyl bromide of formula (II) | m/e value obtained in FD-MASS analysis of the product polyprenylacetone |
|---|---|
| 11 | 1010 |
| 12 | 1078 |
| 13 | 1146 |
| 14 | 1214 |
| 16 | 1350 |
| 17 | 1418 |
| 18 | 1486 |
| 19 | 1554 |

EXAMPLE 2

Synthesis of polyprenylacetone

Methyl acetoacetate (1.40 g) was used in place of ethyl acetoacetate, and the reaction with polyprenyl bromide and the purification of the product were carried out following the procedure of Example 1. There was obtained 2.26 g of a pale yellow oil. NMR analysis, IR analysis and FD-MASS analysis of the oil gave the following results and confirmed that the oil was methyl polyprenylketocarboxylate of formula (IV) in which n=15 and R$^7$=CH$_3$:

IR analysis: 1740, 1720, 1660, 830 cm$^{-1}$.

$^1$H-NMR analysis: $\delta_{CCl_4}^{ppm}$ 3.25

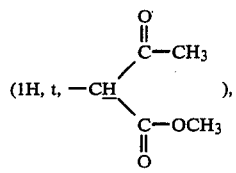

3.78(3H, s, —CO$_2$CH$_3$).

FD-MASS analysis: m/e=1340.

This methyl polyprenylketocarboxylate was saponified and decarboxylated and the product was purified by the procedure of Example 1 to give 1.87 g of a pale yellow oil. The results of IR, $^1$H-NMR and FD-MASS analyses of this oil were in agreement with those obtained with the polyprenylacetone of Example 1.

EXAMPLE 3

Production of a polyprenylacetone mixture

A mixture of polyprenol species of formula (V) as obtained by the procedure of Reference Example 1 and having substantially the same composition as the mixture described in Reference Example 1 with n being distributed between 11 and 19 was converted to a polyprenyl bromide mixture by reacting with pohsphorus tribromide following the procedure of Reference Example 2, and 4.30 g of the bromide mixture was reacted with ethyl acetoacetate following the procedure of Example 1. The thus-produced ethyl polyprenylketocarboxylate mixture was saponified and decarboxylated in the same manner as in Example 1 to give 1.95 g of a pale yellow viscous oil. The results of IR and $^1$H-NMR analyses of this oil were in substantial agreement with those obtained with the polyprenylacetone of Example 1 with respect to the positions of characteristic absorptions and of characteristic signals.

EXAMPLE 4

Synthesis of

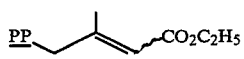

A three-necked flask was charged with 40 ml of anhydrous tetrahydrofuran and 220 mg of 50% sodium hydride, and thereto was added dropwise a solution of 1.0 g of ethyl diethylpohsphonoacetate [(C$_2$H$_5$O)$_2$P(=O)—CH$_2$CO$_2$C$_2$H$_5$] in 10 ml of anhydrous tetrahydorfuran with stirring at room temperature. After completion of the dropping, stirring was continued at room temperature for an additional hour. Then, a solution of 1.92 g of polyprenylacetone of formula (I-1) synthesized in Example 1 (n=15) in 10 ml of anhydrous tetrahydrofuran was added dropwise at room temperature. After completion of the dropping, stirring was further continued at room temperature for 30 minutes and then at 50°–60° C. for 3 hours. The reaction mixture was then cooled to room temperature, about 1 ml of water was added, the solvent was distilled off using a rotary evaporator, and the residue, following addition of about 50 ml of water, was extracted with hexane. The hexane layer was washed with saturated aqueous sodium chloride and dried over anhydrous magnesium sulfate, and the hexane was distilled off to give a brownish yellow oil. The oil was purified by silica gel column chromatography (developing solvent: hexane-ethyl acetate=98:2 by volume) to give 1.62 g of a colorless oil. The analytical results shown below identified this oil as ethyl polyprenylcarboxylate of formula (I-2) in which n=15 and $R^1=C_2H_5$.

IR analysis: 1715, 1640, 1440, 1385, 1210, 1135, 830, 790 cm$^{-1}$.

$^1$H-NMR analysis: $\delta_{CCl_4}^{ppm}$ 1.20(t, 3H), 1.53(s, 9H), 1.62(s, 48H), 1.7–2.4(m, 75H), 4.06(q, 2H), 5.06(br, 18H), 5.56(br, 1H).

FD-MASS analysis: m/e=1352.

Essentially following the above procedure, species of ethyl polyprenylcarboxylate of formula (I-2) in which n=11–19 but other than 15 were prepared from polyprenylacetone species of formula (I-1) having corresponding values of n (synthesized from the corresponding polyprenyl bromide species following the procedure of Example 1). The yields were almost the same as in the case of ethyl polyprenylcarboxylate of formula (I-2) in which n=15. The characteristic absorption on their IR spectra and the characteristic signals on their $^1$H-NMR spectra were in substantial agreement with those for the above-mentioned ethyl polyprenylcarboxylate of formula (I-2) in which n=15 with respect to their positions. The results of FD-MASS analyses were as follows:

| The value of n in the starting polyprenyl-acetone of formula (I-1) | m/e value for the product ethyl polyprenylcarboxylate |
| --- | --- |
| 11 | 1080 |
| 12 | 1148 |
| 13 | 1216 |
| 14 | 1234 |
| 16 | 1420 |
| 17 | 1438 |
| 18 | 1556 |
| 19 | 1624 |

EXAMPLE 5

Synthesis of

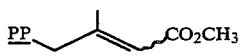

Essentially following the procedure of Example 4 except that 0.98 g of methyl diethylphosphonoacetate was used in place of ethyl diethylphosphonoacetate (1.0 g), there was obtained 1.55 g of methyl polyprenylcarboxylate of formula (I-2) in which n=15 and $R^1=CH_3$. The analytical results for this product are shown below.

$^1$H-NMR analysis: $\delta_{CCl_4}^{ppm}$ 1.53(s, 9H), 1.62(s, 48H), 1.7–2.4(m, 75H), 3.75(s, 3H), 5.05(br, 18H), 5.56 (br, 1H).

FD-MASS analysis: m/e=1338.

Essentially following the above procedure, methyl polyprenylcarboxylate species of formula (I-2) in which n=11–19 but other than 15 were also synthesized.

EXAMPLE 6

Synthesis of

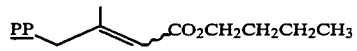

About 10 mg of 50% sodium hydride (as the ester exchange catalyst) was added to a solution of 0.5 g of the ethyl polyprenylcarboxylate of formula (I-2) synthesized in Example 4 (n=15) in about 10 ml of n-butanol, and the mixture was refluxed with stirring for 24 hours and then cooled to room temperature. The solvent was distilled off using a rotary evaporator. There was obtained 0.5 g of a yellow oil, which gave m/e=1380 upon FD-MASS analysis and was thus identified as butyl polyprenylcarboxylate of formula (I-2) in which n=15 and $R^1=n-C_4H_9$.

Essentially following the above procedure, there were also synthesized butyl polyprenylcarboxylate species of formula (I-2) in which n=11–19 but other than 15.

EXAMPLE 7

Synthesis of

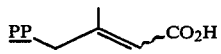

To a solution composed of 0.1 g of sodium hydroxide, 1 ml of water and 9 ml of ethanol was added 0.5 g of the ethyl polyprenylcarboxylate synthesized in Example 4 [formula (I-2), n=15 and $R^1=C_2H_5$], and the mixture was refluxed with stirring for 5 hours. Then, most of the ethanol was distilled off using a rotary evaporator, 10 ml of water was added to the residue, and the resulting mixture was adjusted to pH about 5 with diluted hydrochloric acid and extracted with hexane. The hexane layer was washed with saturated aqueous sodium chloride and dried over anhydrous magnesium sulfate, and the solvent was distilled off to give 0.45 g of a yellow oil. The analytical results as shown below identified this oil as polyprenylcarboxylic acid of formula (I-4) in which n=15.

IR analysis: 3600–2900(weak), 2800–2400(weak), 1685, 1660(shoulder), 1635, 1435, 1370, 1285, 1245, 830 cm$^{-1}$.

$^1$H-NMR analysis: $\delta_{CCl_4}^{ppm}$ 1.53(s, 9H), 1.62(s, 48H), 1.7–2.4(m, 75H), 5.06(br, 18H), 5.56(br, 1H), ~11.5(br, 1H).

Essentially following the above procedure, there were also synthesized polyprenylcarboxylic acid species of formula (I-4) in which n=11–19 but other than 15.

EXAMPLE 8

Synthesis of

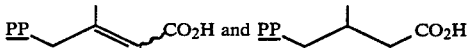

To a solution composed of 0.3 g of sodium hydroxide, 3 ml of water and 20 ml of ethanol was added 1.62 g of the ethyl polyprenylcarboxylate synthesized by the procedure of Example 4 [formula (I-2), n=15 and $R^1=C_2H_5$], and the mixture was refluxed with stirring for 5 hours. Thereafter, most of the ethanol was distilled off using a rotary evaporator, 10 ml of water was added, and the resulting mixture was adjusted to pH about 5 with diluted hydrochloric acid and extracted with hexane. The hexane layer was washed with saturated aqueous sodium chloride and dried over anhydrous magnesium sulfate. The solvent was then distilled off to give a yellow oil. This oil was purified by silica gel column chromatography [developing solvent: hexane-ethyl acetate=90:10 (by volume)] to give 1.42 g of a colorless oil. The analytical results shown below identified this oil as polyprenylcarboxylic acid of formula (I-4) in which n=15.

IR analysis: 3600–2900(weak), 2800–2400(weak), 1685, 1660, 1635, 1435, 1370, 830 cm$^{-1}$.

$^1$H-NMR analysis: $\delta_{CCl_4}^{ppm}$ 1.53(s, 9H), 1.62(s, 48H), 1.7–2.4(m, 75H), 5.06(br, 18H), 5.56(br, 1H), ~11.5(br, 1H).

Then, 1.42 g of this polyprenylcarboxylic acid was selectively hydrogenated by the following procedure. Thus, 0.7 mg of $\mu,\mu'$-dichlorobis(1,5-cyclooctadiene)rhodium(I) and 7.3 mg of neomenthyldiphenylphosphine were were placed in a pressure bottle, and the bottle was evacuated and filled with argon with stirring with a magnetic stirrer. Freshly distilled absolute ethanol (5 ml) was added and the resulting yellow solution was stirred under a hydrogen pressure of 3 atmospheres for 30 minutes. Separately, a solution of 1.42 g of polyprenylcarboxylic acid and 17 mg of sodium methoxide in 4 ml of absolute ethanol was stirred in an argon atmosphere. The thus-prepared catalyst solution and polyprenylcarboxylic acid solution were transferred via cannula to a preliminarily evacuated and argon-filled autoclave, and the hydrogenation reaction was carried out under a hydrogen pressure of 2.5 atmospheres at room temperature for 24 hours. After the reaction, the solution was concentrated using a rotary evaporator, diluted hydrochloric acid was added to the residue, and the mixture was extracted with hexane. The extract was dried over magnesium sulfate and the solvent was distilled off to give 1.40 g of a brownish yellow oil. The oil was purified by silica gel column chromatography [developing solvent: hexane-ethyl acetate=90:10 (by volume)] to give 1.25 g of a colorless viscous oil. The analytical results shown below identified this oil as dihydropolyprenylcarboxylic acid of fomrula (I-5) in which n=15.

IR analysis: 3600–2900(weak), 2800–2400(weak), 1705, 1660, 1440, 1375, 830 cm$^{-1}$.

$^1$H-NMR analysis: $\delta_{CCl_4}^{ppm}$ 1.53(s, 9H), 1.62(s, 48H), 1.7–2.5(m, 76H), 5.06(br, 18H), ~10.0(br, 1H).

*[The signal of $\delta$5.56(br, 1H) found in the starting unsaturated polyprenylcarboxylic acid had disappeared.]

FD-MASS analysis: m/e=1328.

Essentially following the above procedure, there were synthesized dihydropolyprenylcarboxylic acid species of formula (I-5) in which n=11–19 but other than 15 from polyprenylcarboxylic acid species having corresponding n values (synthesized by essentially following the procedure of Example 4). The yields were almost comparable to the yield attained in the synthesis of the dihydropolyprenylcarboxylic acid of formula (I-5) in which n=15. The characteristic absorptions on their IR spectra and the characteristic signals on their $^1$H-NMR spectra were in substantial agreement with those of the above-mentioned dihydropolyprenylcarboxylic acid of formula (I-5) in which n=15 with respect to the positions of the absorptions and signals. The results of FD-MASS analysis were as follows:

| The starting polyprenylcarboxylic acid (I-4) Value of n in formula (I-4) | The product dihydropolyprenylcarboxylic acid m/e value |
|---|---|
| 11 | 1056 |
| 12 | 1124 |
| 13 | 1192 |
| 14 | 1260 |
| 16 | 1396 |
| 17 | 1464 |
| 18 | 1532 |
| 19 | 1600 |

EXAMPLE 9

Synthesis of

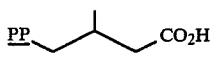

A solution, in 5 ml of tetrahydrofuran, of 1.15 g of the polyprenylcarboxylic acid synthesized by the procedure of Example 7 [formula (I-4), n=15] was added over 2 minutes to a blue solution prepared from 100 mg of lithium and 30 ml of liquid ammonia under nitrogen. Stirring was continued at −33° C. for 30 minutes. Then, 3.0 g of ammonium chloride was added portionwise to decompose the excess lithium. The mixture was allowed to stand overnight for evaporation of ammonia, then 3% hydrochloric acid was added to the residue, and the mixture was extracted with hexane. The hexane layer was dried over magnesium sulfate and the solvent was distilled off using a rotary evaporator to give a yellow oil. Purification by silica gel column chromatography [developing solvent: hexane-ethyl acetate=90:10 (by volume)] gave 1.03 g of dihydropolyprenylcarboxylic acid of formula (I-5) in which n=15. The results of IR, NMR and FD-MASS analysis were in agreement with those of the dihydropolyprenylcarboxylic acid (n=15) obtained in Example 8.

EXAMPLE 10

Synthesis of

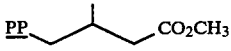

In 20 ml of diethyl ether was dissolved 1.03 g of the dihydropolyprenylcarboxylic acid synthesized by the procedure of Example 8 [formula (I-5), n=15], and a solution of diazomethane in diethyl ether was added, with occasional tracing by thin layer chromatography, until the spot of the starting carboxylic acid was no more detected. The excess diazomethane was decomposed by addition of a small amount of acetic acid, and the reaction product was concentrated using a rotary evaporator to give a yellow oil. This oil was purified by silica gel column chromatography [developing solvent: hexane-ethyl acetate=98:2 (by volume)] to give 1.01 g of a colorless oil. Based on the analytical results shown below, this oil was identified as methyl dihydropolyprenylcarboxylate of formula (I-3) in which n=15 and $R^6=CH_3$.

IR analysis: 1735, 1660, 1440, 1375, 830 cm$^{-1}$.

$^1$H-NMR analysis: $\delta_{CCl_4}^{ppm}$ 1.53(s, 9H), 1.62(s, 48H), 1.72–2.5(m, 76H), 3.68(s, 3H), 5.06(br, 18H).

FD-MASS analysis: m/e=1342.

Essentially following the above procedure, methyl dihydropolyprenylcarboxylate species of formula (I-3) in which n=11–19 but other than 15 and $R^6$=CH$_3$ could be synthesized from dihydropolyprenylcarboxylic acid species of formula (I-5) having the corresponding values of n.

EXAMPLE 11

Synthesis of

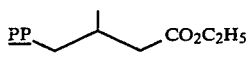

In 20 ml of anhydrous ethanol was dissolved 0.50 g of the methyl dihydropolyprenylcarboxylate synthesized in Example 10 [formula (I-3), n=15 and $R^6$=CH$_3$], then 10 mg of 50% sodium hydride was added thereto, and the mixture was refluxed for 14 hours. After cooling, the ethanol was distilled off using a rotary evaporator, water was added to the residue, the mixture was extracted with hexane, and the extract was dried over magnesium sulfate. The hexane was distilled off using a rotary evaporator to give 0.43 g of a pale yellow oil. FD-MASS analysis of this oil gave m/e=1356 and confirmed that said oil was ethyl dihydropolyprenylcarboxylate of formula (I-3) in which n=15 and $R^6$=C$_2$H$_5$.

Essentially following the above procedure, there also could be synthesized ethyl dihydropolyprenylcarboxylate species of formula (I-3) in which $R^6$=C$_2$H$_5$ and n=11–19 but other than 15.

EXAMPLE 12

Synthesis of

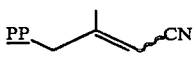

A three-necked flask was charged with 40 ml of anhydrous tetrahydrofuran and 220 mg of 50% sodium hydride, and thereto was added dropwise with stirring a solution of 1.0 g of diethylphosphonoacetonitrile in 10 ml of anhydrous tetrahydrofuran. After completion of the dropping, the mixture was further stirred at room temperature for an hour. Then, a solution of 1.92 g of polyprenylacetone of formula (I-1) in which n=15 in 10 ml of anhydrous tetrahydrofuran was added dropwise at room temperature, and after completion of the dropping, stirring was continued at room temperature for 30 minutes and then further at 50°–60° C. for 3 hours. Thereafter, the reaction mixture was cooled to room temperature, about 1 ml of water was added, the tetrahydrofuran was distilled off from the reaction mixture using a rotary evaporator, about 50 ml of water was added to the residue, and the resulting mixture was extracted with hexane. The extract was washed with saturated aqueous sodium chloride solution and dried over anhydrous magnesium sulfate and the hexane was distilled off to give a brownish yellow oil. Purification of this oil by silica gel column chromatography [developing solvent: hexane-ethyl acetate=98:2 (by volume)] gave 1.72 g of a colorless oil. The analytical results shown below confirmed that the oil was polyprenylnitrile of formula (I-6) in which n=15.

IR analysis: 2220, 1660(weak), 1625, 1440, 1375, 830 cm$^{-1}$.

$^1$H-NMR analysis: $\delta_{CCl_4}^{ppm}$ 1.53(s, 9H), 1.62(s, 48H) 1.7–2.5(m, 75H), 5.05(br, 19H).

FD-MASS analysis: m/e=1305.

Essentially following the above procedure, polyprenylnitrile species of formula (I-6) in which n=11–19 but other than 15 were synthesized from polyprenylacetone species of formula (I-1) having corresponding values of n (synthesized by essentially following the procedure of Example 1). For each of said species, the yield was comparable to that attained in the synthesis of the polyprenylnitrile of formula (I-6) in which n=15, and the characteristic absorptions on its IR spectrum and the characteristic signals on its NMR spectrum were substantially identical with those of the above-mentioned polyprenylnitrile of formula (I-6) in which n=15 with respect to the positions of the absorptions and signals. The results of FD-MASS analysis were as follows:

| Starting polyprenyl-<br>acetone (I-1)<br>Value of n in formula (I-1) | Product polyprenyl-<br>nitrile<br>Value of m/e |
| --- | --- |
| 11 | 1033 |
| 12 | 1101 |
| 13 | 1169 |
| 14 | 1237 |
| 16 | 1373 |
| 17 | 1441 |
| 18 | 1509 |
| 19 | 1577 |

EXAMPLE 13

Synthesis of

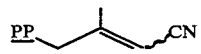

Using dimethylphosphonoacetonitrile (0.84 g) as the Wittig reagent in place of diethylphosphonoacetonitrile (1.0 g), the same procedure as in Example 12 was carried out to give 1.70 g of colorless oil. The results of IR analysis, $^1$H-NMR analysis and FD-MASS analysis of this oil were in complete agreement with those of the polyprenylnitrile of formula (I-6) (n=15) obtained in Example 12.

EXAMPLE 14

Synthesis of

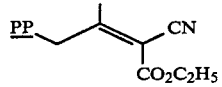

A three-necked flask was charged with 50 ml of benzene, 173 mg of ethyl cyanoacetate, 35 mg of ammonium acetate, 35 mg of acetic acid and 1.96 g of polyprenylacetone of formula (I-1) in which n=15, synthesized by the procedure of Example 1, and the mixture was heated at the boiling point of the solvent for 10 hours while distilling off the by-product water from the system azeotropically with benzene. Then, the reaction mixture was cooled to room temperature and washed with water in a separatory funnel and dried over anhydrous magnesium sulfate. After the solvent was distilled off, there was obtained a yellow oil. Purification of the oil by silica gel column chromatography [developing solvent: hexane-ethyl acetate=98:2 (by volume)] gave 1.42 g of a colorless oil. The analytical results shown below served for the identification of this oil as a polyprenyl compound of formula (I-8) in which n=15 and $n^2=C_2H_5$.

IR analysis: 2220, 1725, 1660, 1600, 1440, 1370, 1275, 1220, 1060, 830 cm$^{-1}$.

$^1$H-NMR analysis: $\delta_{CCl_4}{}^{ppm}$ 1.30(t, 3H), 1.53(s, 9H), 1.62(s, 48H), 1.7–2.5(m, 75H), 4.20(q, 2H), 5.06 (br, 18H).

FD-MASS analysis: m/e=1377.

Essentially following the above procedure, species of the polyprenyl compound of formula (I-8) in which n=11, 12, 13, 14, 16, 17, 18 and 19, respectively, and $R^2=C_2H_5$ were synthesized from the corresponding polyprenylacetone species of formula (I-1) in which n=11–19 but other than 15 (synthesized by essentially following the procedure of Example 1). For each species, the yield was comparable to that attained in the synthesis of the above-mentioned polyprenyl compound of formula (I-8) in which n=15, and the characteristic absorptions on its infrared absorption spectrum and the characteristic signals on its $^1$H-NMR spectrum were in substantial agreement with those of the above-mentioned polyprenyl compound of formula (I-8) in which n=15 and $R^2=C_2H_5$ with respect to the positions of the absorptions and signals. The results of FD-MASS analysis were as follows:

| Starting polyprenylacetone Value of n in formula (I-1) | Product polyprenyl compound Value of m/e |
|---|---|
| 11 | 1105 |
| 12 | 1173 |
| 13 | 1241 |
| 14 | 1309 |
| 16 | 1445 |
| 17 | 1513 |
| 18 | 1581 |
| 19 | 1649 |

EXAMPLE 15

Synthesis of

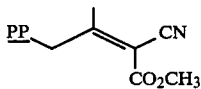

Using 152 mg of methyl cyanoacetate in place of ethyl cyanoacetate, the same procedure as in Example 14 was carried out to give 1.41 g of a colorless oil. Based on the analytical results shown below, this oil was identified as the polyprenyl compound of formula (I-8) in which n=15 and $R^2=CH_3$.

NMR analysis: $\delta_{CCl_4}{}^{ppm}$ 1.53(s, 9H), 1.62(s, 48H), 1.7–2.5(m, 75H), 3.68(s, 3H), 5.05(br, 18H).

FD-MASS analysis: m/e=1363.

EXAMPLE 16

Synthesis of

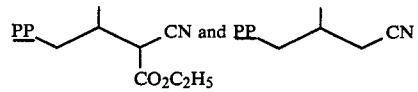

A three-necked flask was charged with 1.40 g of the compound of formula (I-8) in which n=15 and $R^2=C_2H_5$ [synthesized in Example 14] and 20 ml of isopropanol. About 50 mg of sodium borohydride was added thereto with stirring at room temperature, and the mixture was stirred at the same temperature for an hour, then poured into about 50 ml of saturated aqueous ammonium chloride and extracted with hexane. The hexane layer was dried over anhydrous magnesium sulfate, and the solvent was distilled off to give 1.35 g of a colorless oil. The analytical results shown below confirmed that this oil was the dihydropolyprenyl-cyanocarboxylic acid ester of formula (I-9) in which n=15 and $R^2=C_2H_5$.

IR analysis: 2245, 1740, 1660, 1440, 1370, 1295, 1240, 1185, 1175, 1020, 830 cm$^{-1}$.

$^1$H-NMR analysis: $\delta_{CCl_4}{}^{ppm}$ 1.04(dd, 3H), 1.30(t, 3H), 3.36(dd, 1H), 4.22(q, 2H), 5.05(br, 18H).

FD-MASS analysis: m/e=1379.

To the above oil, there were added a mixture of 30 ml of ethanol, 3 ml of water and 0.3 g of sodium hydroxide, and the mixture was stirred at room temperature for an hour. Then, 100 ml of water was added, followed by portionwise addition of 6N hydrochloric acid so as to adjust pH to 2. The whole mixture was extracted with three portions of ether. The organic layers were combined, washed with water and saturated aqueous sodium chloride and then dried over anhydrous magnesium sulfate, and the solvent was distilled off to give 1.22 g of an oil.

Then, the oil was dissolved in 20 ml of pyridine, 0.1 g of copper dust was added, and the mixture was refluxed for 2 hours. The copper dust was filtered off and washed with hexane. The filtrate and the washings were combined, most of the solvent was removed using a rotary evaporator the residue was dissolved in hexane, the solution was washed with saturated aqueous sodium chloride and dried over anhydrous magnesium sulfate, and the solvent was distilled off, to give a yellow oil. Purification of the oil by silica gel column chromatography [developing solvent: hexane-ethyl acetate=98:2 (by volume)] yielded 1.01 g of a colorless oil. The analytical data shown below served for the identification of this oil as the dihydropolyprenylnitrile of formula (I-7) in which n=15.

IR analysis: 2245, 1660, 1440, 1375, 830 cm$^{-1}$.

$^1$H-NMR analysis: $\delta_{CCl_4}{}^{ppm}$ 1.00(d, 3H), 1.1–1.5(m, 2H), 1.53(s, 9H), 1.62(s, 48H), 1.7–2.5(m, 73H), 5.05 (br, 18H).

FD-MASS analysis: m/e=1307.

Dihydropolyprenylnitrile species of formula (I-7) in which n=11, 12, 13, 14, 16, 17, 18 and 19, respectively were synthesized by essentially following the above procedure. For each dihydropolyprenylnitrile species, the characteristic absorptions on its infrared absorption spectrum and the characteristic signals on its $^1$H-NMR spectrum were in substantial agreement with those of the dihydropolyprenylnitrile of formula (I-7) in which n=15. The FD-MASS analytical data were as follows:

| Starting polyprenylacetone Value of n in formula (I-1) | Product dihydropolyprenylnitrile Value of m/e |
|---|---|
| 11 | 1035 |
| 12 | 1103 |
| 13 | 1171 |
| 14 | 1239 |
| 16 | 1375 |
| 17 | 1443 |
| 18 | 1511 |
| 19 | 1579 |

EXAMPLE 17

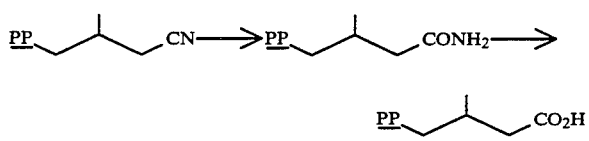

A three-necked flask was charged with 1.30 g of the dihydropolyprenylnitrile of formula (I-7) (n=15) synthesized by the procedure of Example 16, under a nitrogen atmosphere, and then the nitrile was dissolved by adding 2 ml of dimethyl sulfoxide distilled in the presence of calcium hydride. Thereto was added 200 mg of sodium superoxide preliminarily pulverized under a nitrogen atmosphere, and the mixture was stirred at room temperature for 7 hours and then poured into ice water. The whole mixture was extracted with three portions of ether. The organic layers were combined, washed well with water and then with saturated aqueous sodium chloride, and dried over anhydrous sodium sulfate, and the solvent was distilled off to give 1.10 g of a yellow oil. Purification of the oil by silica gel column chromatography [developing solvent: hexane-ethyl acetate=90:10 (by volume)] gave 0.92 g of a colorless oil. The analytical results shown below served for the identification of this product as the polyprenylamide of formula (I-11) in which n=15.

IR analysis: ~3350, 3100, 1660, 1650, 1440, 1375, 830 cm$^{-1}$.

$^1$H-NMR analysis: $\delta_{ppm}^{CCl_4}$ 0.91(d, 3H), 1.60(s, 9H), 1.68 (s, 48H), 5.05(br, 18H), 6.70(br, 1H), 7.22(br, 1H).

FD-MASS analysis: m/e=1325.

Essentially following the above procedure, polyprenylamide species of formula (I-11) in which n=11-19 but other than 15 were synthesized from dihydropolyprenylnitrile species of formula (I-7) having corresponding value of n. For each polyprenylamide species, the yield was comparable to that attained in the synthesis of the polyprenylamide with n=15, and the characteristic absorptions on its infrared absorption spectrum and the characteristic signals on its $^1$H-NMR spectrum were in substantial agreement with those of the above-mentioned polyprenylamide of formula (I-11) in which n=15.

To a solution composed of 0.1 g of sodium hydroxide, 1 ml of water and 9 ml of ethanol was added 0.50 g of the above-synthesized polyprenylamide of formula (I-11) in which n=15, the mixture was refluxed for 5 hours, then the ethanol was distilled off under reduced pressure, 10 ml of water was added, the pH was adjusted to about 5 by adding diluted hydrochloric acid, and the whole mixture was extracted with three portions of diethyl ether. The organic layers were combined, washed with water and saturated aqueous sodium chloride and dried over anhydrous magnesium sulfate, and the solvent was distilled off to give 0.45 g of a yellow oil. Purification of the oil by silica gel column chromatography [developing solvent: hexane-ethyl acetate=90:10 (by volume)] gave 0.40 g of the dihydropolyprenylcarboxylic acid of formula (I-5) in which n=15. The results of IR analysis, NMR analysis and FD-MASS analysis were in agreement with those for the dihydropolyprenylcarboxylic acid (n=15) obtained in Example 8.

Essentially following the above procedure, dihydropolyprenylcarboxylic acid species of formula (I-5) in which n=11-19 but other than 15 were synthesized from polyprenylamide species of formula (I-11) having corresponding values of n. For each product species, the yield was comparable to that attained in the synthesis of the dihydropolyprenylcarboxylic acid with n=15, and the results of IR analysis, NMR analysis and FD-MASS analysis were in agreement with those of the corresponding dihydropolyprenylcarboxylic acid species obtained in Example 8.

EXAMPLE 18

Synthesis of

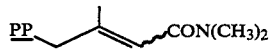

A three-necked flask was charged with 40 ml of anhydrous tetrahydrofuran and 220 mg of 50% sodium hydride, and thereto was added dropwise with stirring at room temperature a solution of 1.1 g of diethylphosphono-N,N-dimethylacetamide in 10 ml of anhydrous tetrahydrofuran. After completion of the addition, stirring was continued at room temperature for an hour. Then, a solution of 1.95 g of the polyprenylacetone of formula (I-1) (n=15) synthesized by the procedure of Example 1 in 10 ml of anhydrous tetrahydrofuran was added dropwise at room temperature. After the addition, the mixture was stirred at room temperature for 30 minutes and then at 50°-60° C. for further 3 hours. Then, the reaction mixture was cooled to room temperature, about 1 ml of water was added, the tetrahydrofuran was distilled off from the reaction mixture using a rotary evaporator, about 50 ml of water was added to the residue, and the resulting mixture was extracted with hexane. The hexane layer was washed with saturated aqueous sodium chloride and dried over anhydrous magnesium sulfate, and the hexane was distilled off, to give a brownish yellow oil. Purification of the oil by silica gel column chromatography [developing solvent: hexane-ethyl acetate=97:3 (by volume)] gave 1.38 g of a colorless oil. Based on the analytical results shown below, this was identified as the polyprenylamide of formula (I-12) in which n=15 and $R^3=R^4=CH_3$.

IR analysis: 1660(shoulder), 1620, 1440, 1370, 1260, 1120, 830 cm$^{-1}$.

$^1$H-NMR analysis: $\delta_{CCl_4}^{ppm}$ 1.53(s, 9H), 1.62(s, 48H), 1.7-2.5(m, 75H), 2.94(s, 6H), 5.05(br, 18H), 5.72 (br, 1H).

FM-MASS analysis: m/e=1351.

Essentially following the above procedure, polyprenylamide species of formula (I-12) in which $R^3=R^4=CH_3$ and $n=11, 12, 13, 14, 16, 17, 18$ and 19, respectively, were synthesized from corresponding polyprenylacetone species of formula (I-1) in which $n=11-19$ but other than 15 (synthesized by essentially following the procedure of Example 1). For each amide species, the characteristic absorptions on its infrared absorption spectrum and the characteristic signals on its $^1$H-NMR spectrum were in agreement with those for the above-mentioned polyprenylamide of formula (I-12) in which $R^3=R^4=CH_3$ and $n=15$ with respect to the positinos of the absorptions and signals.

EXAMPLE 19

Synthesis of

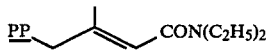

The procedure of Example 18 was followed except that 1.2 g of diethylphosphono-N,N-diethylacetamide was used as the Wittig reagent in place of 1.1 g of diethylphosphono-N,N-dimethylacetamide. As the final product, there was obtained 1.40 g of a colorless oil. Based on the analytical data shown below, this oil was identified as the polyprenylamide of formula (I-12) in which $n=15$ and $R^3=R^4=C_2H_5$.

IR analysis: 1660(shoulder), 1620, 1440, 1370, 1260, 1120, 830 cm$^{-1}$.

NMR analysis: $\delta_{CCl_4}^{ppm}$ 1.05(t, 6H), 1.53(s, 9H), 1.62 (s, 48H), 1.7-2.5(m, 75H), 3.26(q, 4H), 5.05(br, 18H), 5.72(br, 1H).

FD-MASS analysis: m/e=1379.

Essentially following the above procedure, polyprenylamide species of formula (I-12) in which $R^3=R^4=C_2H_5$ and $n=11, 12, 13, 14, 16, 17, 18$ and 19, respectively, were synthesized from corresponding polyprenylacetone species of formula (I-1) in which $n=11-19$ but other than 15 (synthesized by essentially following the procedure of Example 1). For each amide species, the characteristic absorptions on its infrared absorption spectrum and the characteristic signals on its $^1$H-NMR spectrum were in agreement with those of the above-mentioned polyprenylamide of formula (I-12) in which $R^3=R^4=C_2H_5$ and $n=15$ with respect to the positions of the absorptions and signals.

EXAMPLE 20

Synthesis of

The procedure of Example 18 was followed except that 1.3 g of diethylphosphono-N,N-dibutylacetamide was used in place of the Wittig reagent used in Example 18. As the final product, there was obtained 1.42 g of a colorless oil. The IR analysis data for this oil were almost identical with those for the polyprenylamide obtained in Example 19. FD-MASS analysis gave a value m/e=1435. Based on these data, the oil was identified as the polyprenylamide of formula (I-12) in which $n=15$ and $R^3=R^4=C_4H_9$.

Essentially following the above procedure, polyprenylamide species of formula (I-12) in which $R^3=R^4=C_4H_9$ and $n=11, 12, 13, 14, 16, 17, 18$ and 19, respectively, were synthesized from corresponding polyprenylacetone species of formula (I-1) in which $n=11-19$ but other than 15 (synthesized by essentially following the procedure of Example 1). For each of said polyprenylamide species, the characteristic absorptions on its infrared absorption spectrum were in good agreement with those of the above-mentioned polyprenylamide of formula (I-12) in which $R^3=R^4=C_4H_9$ and $n=15$. FD-MASS analysis gave m/e values different from the value for the homolog with $n=15$ by values corresponding to respective differences in the number of isoprene units.

EXAMPLE 21

Synthesis of

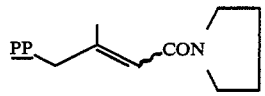

The procedure of Example 18 was followed except that 1.1 g of diethylphosphono-N,N-tetramethyleneacetamide was used in place of the Wittig reagent used in Example 18. As the final product, there was obtained 1.38 g of a colorless oil. Based on the analytical data shown below, this oil was identified as the polyprenylamide of formula (I-12) in which $n=15$ and $R^3+R^4=-(CH_2)_4-$.

IR analysis: 1660(shoulder), 1620, 1440, 1370, 1260, 1120, 830 cm$^{-1}$.

$^1$H-NMR analysis: $\delta_{CCl_4}^{ppm}$ 1.5-2.7(136H) including 1.53(s) and 1.62(s), 3.3-3.8(m, 4H), 5.05(br, 18H), 5.73 (br, 1H).

FD-MASS analysis: m/e=1377.

Essentially following the above procedure, polyprenylamide species of formula (I-12) in which $R^3+R^4=-(CH_2)_4-$ and $n=11, 12, 13, 14, 16, 17, 18$ and 19, respectively, were synthesized from corresponding polyprenylacetone species of formula (I-1) in which $n=11-19$ but other than 15 (synthesized by essentially following the procedure of Example 1). For each amide species, the characteristic absorptions on its infrared absorption spectrum and the characteristic signals on its $^1$H-NMR spectrum were in agreement with those of the above-mentioned polyprenylamide of formula (I-12) in which $n=15$ and $R^3+R^4=-(CH_2)_4-$ with respect to the positions of the absorptions and signals.

EXAMPLE 22

Synthesis of

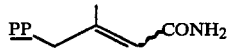

The procedure of Example 18 was followed except that 1.0 g of diethylphosphonoacetonitrile was used in place of the Wittig reagent used in Example 18, to give 1.52 g of a colorless oil. Based on the analytical data shown below, this oil was identified as the polyprenylnitrile of formula (I-6) in which $n=15$.

IR analysis: 2220, 1660(weak), 1625, 1440, 1375, 830 cm$^{-1}$.

$^1$H-NMR analysis: $\delta_{CCl_4}^{ppm}$ 1.53(s, 9H), 1.62(s, 48H), 1.7-2.5(m, 75H), 5.05(br, 19H).

This polyprenylnitrile was dissolved in 50 ml of methylene chloride, and 20 g of activated manganese dioxide was added in a nitrogen atmosphere, followed by vigorous stirring for 48 hours. The reaction mixture was filtered through a Nutsche funnel packed with Celite and the solvent was distilled off using a rotary evaporator to give a brown oil. Purification of the oil by silica gel column chromatography [developing solvent: hexane:ethyl acetate=98:2 (by volume)] gave 0.34 g of a colorless oil. Based on the analytical data shown below, this oil was identified as the polyprenylamide of formula (I-10) in which n=15.

IR analysis: ~3350, 3100, 1670, 1610, 1440, 1370, 1140, 830 cm$^{-1}$.

$^1$H-NMR analysis: $\delta_{CCl_4}{}^{ppm}$ 1.53(s, 9H), 1.62(s, 48H), 1.7–2.5 (m, 75H), 5.05(br, 18H), 5.72(br, 1H), 6.73(br, 1H), 7.20(br, 1H).

FD-MASS analysis: m/e=1323.

Essentially following the above procedure, polyprenylamide species of formula (I-10) in which n=11, 12, 13, 14, 16, 17, 18 and 19, respectively, were synthesized from corresponding polyprenylnitrile species of formula (I-6) in which n=11–19 but other than 15. For each amide species, the characteristic absorptions on its infrared absorption spectrum and the characteristic signals on its $^1$H-NMR spectrum were in agreement with those of the above-mentioned polyprenylamide of formula (I-10) in which n=15 with respect to the positions of the absorptions and signals.

EXAMPLE 23

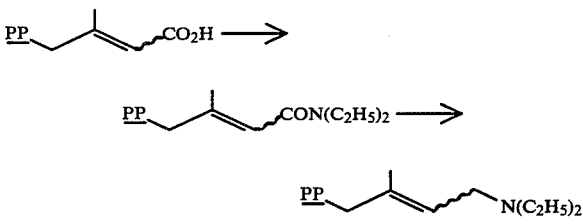

A reaction vessel was charged with 1.32 g of the polyprenylcarboxylic acid of formula (I-4) in which n=15 (synthesized by the procedure of Example 7) and 10 ml of methylene chloride. Thereto was added gradually 206 mg of N,N'-dicyclohexylcarbodiimide with ice-water cooling, followed by stirring for 15 minutes. Then, a solution of 73 mg of diethylamine [formula (IX), R$^3$=R$^4$=C$_2$H$_5$] in 2 ml of methylene chloride was added dropwise gradually using a syringe. The reaction mixture was warmed to room temperature with stirring, then the floating soild was filtered off, and the filtrate was poured into 10 ml of cold water. The organic layer separated was washed in sequence with 3% hydrochloric acid, water, saturated aqueous sodium bicarbonate and saturated aqueous sodium chloride, and dried over anhydrous magnesium sulfate. The solvent was distilled off under reduced pressure to give a yellow oil. Purification of the oil by silica gel column chromatography [developing solvent: hexane-ethyl acetate=97:3 (by volume)] gave 1.12 g of a colorless oil. The analytical data shown below served for the identification of this oil as the polyprenylamide of formula (I-12) in which n=15 and R$^3$=R$^4$=C$_2$H$_5$.

IR analysis: 1660(shoulder), 1620, 1440, 1370, 1260, 1120, 830 cm$^{-1}$.

NMR analysis: $\delta_{CCl_4}{}^{ppm}$ 1.05(t, 6H), 1.53(s, 9H), 1.62 (s, 48H), 1.7–2.5(m, 75H), 3.26(q, 4H), 5.05(br, 18H), 5.72(br, 1H).

FD-MASS analysis: m/e=1379.

A three-necked flask was charged with 10 ml of anhydrous diethyl ether and 40 mg of lithium aluminum hydride, and a solution of 1.10 g of the above polyprenylamide in 5 ml of anhydrous diethyl ether was added dropwise with ice-water cooling, followed by reflux for 5 hours. With ice-water cooling and stirring, there was added 90 mg of water. Stirring was continued under said conditions for 30 minutes. The reaction mixture was filtered through a glass filter, the white residue was washed well with diethyl ether. The filtrate and the washings were combined and the solvent was distilled off under reduced pressure to give a pale yellow oil. Purification of the oil by silica gel column chromatography [developing solvent: hexane-ethanol=95:5 (by volume)] gave 0.91 g of a colorless oil. The analytical data shown below demonstrated that this oil was the polyprenylamine of formula (I-4) in which n=15 and R$^3$=R$^4$=C$_2$H$_5$.

IR analysis: 1660, 1440, 1375, 1190, 1160, 1060, 1050, 830 cm$^{-1}$.

$^1$H-NMR analysis: $\delta_{CCl_4}{}^{ppm}$ 0.93(t, 6H), 1.5–1.8(60H), 1.8–2.3(m, 72H), 2.38(q, 4H), 2.92(d, 2H), 4.9–5.3 (br, 19H).

FD-MASS analysis: m/e=1365.

By essentially the same procedure as above, polyprenylamine species of formula (I-14) in which R$^3$=R$^4$=C$_2$H$_5$ and n=11, 12, 13, 14, 16, 17, 18 and 19, respectively, were synthesized from corresponding polyprenylcarboxylic acid species of formula (I-4) in which n=11–19 but other than 15. For each amine species, the yield was comparable to that attained in the synthesis of the above-mentioned polyprenylamine of formula (I-14) in which n=15 and R$^3$=R$^4$=C$_2$H$_5$ and the characteristic absorptions on its infrared absorption spectrum and the characteristic signals on its $^1$H-NMR spectrum were in agreement with those of the above-mentioned polyprenylamine of formula (I-14) in which n=15 and R$^3$=R$^4$=C$_2$H$_5$ with respect to the positions of the absorptions and signals.

FD-MASS analysis gave m/e values different from the value for the homolog in which n=15 by values corresponding to respective differences in the number of isoprene units.

EXAMPLES 24–29

Synthesis of

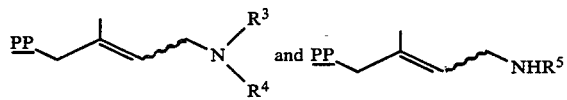

The procedure of Example 23 was followed using 1.32 g (1 mmol) of the polyprenylcarboxylic acid of formula (I-4) in which n=15 (synthesized by essentially following the procedure of Example 7) and the amine of formula (IX) or (X) (1 mmol). Via the amide of formula (I-12) or (I-13), there was synthesized the polyprenylamine of formula (I-14) or (I-15), respectively, in which n=15 as the final product. The substituents R$^3$, R$^4$ and R$^5$ in the starting amines are indicated below together with the yields of the corresponding polyprenylamine products.

| Example | Amine of formula (IX) | Polyprenylamine of formula (I-14) |
|---|---|---|

-continued

| No. | R³ | R⁴ | Yield (g) |
|---|---|---|---|
| 24 | CH₃ | CH₃ | 0.87 |
| 25 | n-C₄H₉ | n-C₄H₉ | 0.94 |
| 26 | —(CH₂)₄— | | 0.85 |
| 27 | C₆H₅CH₂ | C₆H₅CH₂ | 0.97 |

| | Amine of formula (X) R⁵ | Polyprenylamine of formula (I-15) |
|---|---|---|
| 28 | C₆H₅ | 0.88 |
| 29 | cyclo-C₆H₁₁ | 0.84 |

The analytical data for each of the above polyprenylamines are shown below:

Polyprenylamine of Example 24 ($R^3=R^4=CH_3$).
IR analysis: 1660, 1440, 1375, 1170, 1035, 1010, 830 cm⁻¹.
¹H-NMR analysis: $\delta_{CCl_4}^{ppm}$ 1.5–1.8(60H), 1.8–2.2(m, 72H), 2.17(s, 6H), 2.83(d, 2H), 4.9–5.3(br, 19H).
FD-MASS analysis: m/e=1337.

Polyprenylamine of Example 25 ($R^3=R^4=$n—$C_4H_9$).
IR analysis: 1660, 1440, 1375, 1190, 1160, ~1050, 830 cm⁻¹.
¹H-NMR analysis: $\delta_{CCl_4}^{ppm}$ 0.7–2.3(150H) including 1.53(s) and 1.62(s), 2.94(d, 2H), 4.9–5.3(br, 19H).
FD-MASS analysis: m/e=1421.

Polyprenylamine of Example 26 [$R^3+R^4=$–(CH₂)₄–].
IR analysis: 1660, 1440, 1375, 1185, 1160, ~1045, 830 cm⁻¹.
¹H-NMR analysis: $\delta_{CCl_4}^{ppm}$ 1.5–2.2(136H) including 1.53(s) and 1.62(s), 2.2–2.7(m, 4H), 2.93(d, 2H), 4.9–5.3 (br, 19H).
FD-MASS analysis: m/e=1363.

Polyprenylamine of Example 27 ($R^3=R^4=CH_2C_6H_5$).
IR analysis: 1660, 1600, 1495, 1440, 1370, 1250, 1115, 1030, 990, 970, 830, 750, 690 cm⁻¹.
¹H-NMR analysis: $\delta_{CCl_4}^{ppm}$ 1.5–1.8(60H), 1.8–2.2(m, 72H), 2.92(d, 2H), 3.58(s, 4H), 4.9–5.3(br, 19H), 7.1–7.6 (m, 10H).
FD-MASS analysis: m/e=1489.

Polyprenylamine of Example 28 ($R^5=C_6H_5$).
IR analysis: 1660, 1605, 1515, 1440, 1370, 830, 750, 690 cm⁻¹.
¹H-NMR analysis: $\delta_{CDCl_3}^{ppm}$ 1.5–1.8(60H), 1.8–2.2(72H), 3.6–3.8

4.9–5.3(br, 19H), 6.4–7.4(m, 5H).

Polyprenylamine of Example 29 ($R^5=$cyclo—$C_6H_{11}$).
IR analysis: 1660, 1440, 1370, 1140, 1125, 830 cm⁻¹.
¹H-NMR analysis: $\delta_{CDCl_3}^{ppm}$ 1.0–2.3(144H) including 1.53 (s) and 1.62(s), 3.25(d, 2H), 4.9–5.3(br, 19H).

Whereas, in the above Examples 24–29, the production of several polyprenylamines of formulas (I-14) and (I-15) in which n=15 and their physical characteristics have been described, polyprenylamine species of formulas (I-14) and (I-15) in which R³ and R⁴, and R⁵ were the same as in Examples 24–29 and n=11, 12, 13, 14, 16, 17, 18 and 19 were also synthesized by essentially following the procedure of Examples 24–29 using polyprenylcarboxylic acid species of formula (I-4) in which n=11–19 but other than 15 and the same amines as used in Examples 24–29. For each product amine species, the characteristic absorptions on its infrared absorption spectrum and the characteristic signals on its ¹H-NMR spectrum were in good agreement with those for the corresponding polyprenylamines with n=15 synthesized in Examples 24–29 with respect to the positions of the absorptions and signals, and the m/e values given by FD-MASS analysis differed from the values for the corresponding homologs with n=15 synthesized in Examples 24–29 by values corresponding to the respective differences in the number of isoprene units.

EXAMPLE 30

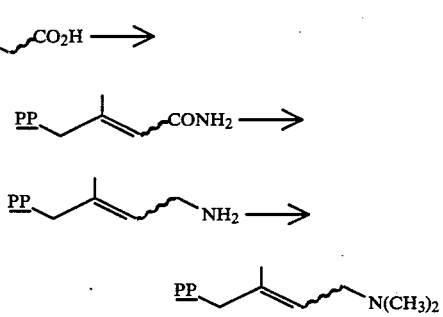

A three-necked flask was charged with 48 mg of 50% sodium hydride and 10 ml of anhydrous benzene, and a solution of 1.32 g of the polyprenylcarboxylic acid of formula (I-4) in which n=15 (synthesized by the procedure of Example 7) in 5 ml of benzene was added dropwise. The mixture was heated at 50° C. for 10 minutes and then cooled to room temperature. Thereto was added portionwise 127 mg of oxalyl chloride using a syringe, the mixture was heated at 50° C. for 30 minutes, then cooled, and filtered, and the filtrate was concentrated under reduced pressure to give 1.33 g of a yellow oil. The oil was dissolved in 10 ml of acetone, 150 mg of ammonium acetate was added, the mixture was stirred vigorously at room temperature for an hour and then filtered, and the filtrate was concentrated under reduced pressure. The residue was dissolved in diethyl ether, the solution was washed with saturated aqueous sodium chloride and dried over anhydrous magnesium sulfate, and the solvent was distilled off under reduced pressure to give a yellow oil. Purification of the oil by silica gel column chromatography [developing solvent: hexane-ethyl acetate=95:5 (by volume)] gave 0.78 g of a colorless oil. The analytical data obtained supported the identification of the oil as the polyprenylamide of formula (I-10) in which n=15.

A three-necked flask was charged with 0.75 g of the above polyprenylamide and 10 ml of anhydrous diethyl ether. Thereafter, the procedure of Example 23 was followed to give 0.54 g of a colorless oil. Based on the analytical data shown below, this oil was identified as the polyprenylamine of formula (I-14) in which n=15 and $R^3=R^4=H$.

IR analysis: 3360, 3280, 1660, 1580, 1440, 1370, 1100, 820, 780 cm⁻¹.
¹H-NMR analysis: $\delta_{CCl_4}^{ppm}$ 1.35(br, 2H, —N$\underline{H}_2$), 1.55(s, 9H), 1.64(s, 51H), 1.8–2.3(72H), 3.12(d, 2$\underline{H}$), 4.9–5.3(br, 19H).

A three-necked flask was charged with 0.50 g of the above polyprenylamine, 130 mg of sodium hydrogen carbonate, 180 mg of methyl iodide and 5 ml of methanol, and the mixture was refluxed with stirring for 72 hours, with addition of two 50-mg portions of methyl iodide after 24 and 48 hours of stirring. The reaction mixture was concentrated under reduced pressure, the residue was extracted with three 5-ml portions of hot chloroform, and the solvent was distilled off under reduced pressure to give 0.43 g of a brownish yellow oil. This oil was identified as the polyprenyltrimethylammonium salt of the formula

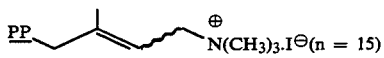

based on the $^1$H-NMR analysis results shown below.

$^1$H-NMR analysis: δppm (DMSO-d$_6$) 1.53(s, 9H), 1.60(s, 48H), 1.65-2.3(75H), 3.00(s, 9H), 3.88(d, 2H), 5.05 (br, 18H), 5.40(br, t, 1H).

A three-necked flask was charged with 60 mg of lithium aluminum hydride and 5 ml of anhydrous tetrahydrofuran, and the contents were refluxed for an hour. After cooling to room temperature, the above polyprenyltrimethylammonium salt (0.40 g) was added all at once and refluxing was continued with vigorous stirring until the evolution of methane was no more observable. After cooling, 0.15 ml of water was added portionwise carefully, then 10 ml of diethyl ether was added, and the mixture was refluxed for 2 hours. After cooling, the white precipitate was filtered off and washed well with several portions of tetrahydrofuran, and the filtrate and the washings were combined and concentrated. The residue was dissolved in diethyl ether, the solution was washed with saturated aqueous sodium chloride and dried over anhydrous potassium carbonate, and the solvent was distilled off under reduced pressure to give a yellow oil. Purification of the oil by silica gel column chromatography [developing solvent:hexane-ethanol=95:5 (by volume)] gave 0.14 g of a yellow oil. As a result of analyses, this product was identified as the same polyprenylamine of formula (I-14) in which n=15 and R$^3$=R$^4$=CH$_3$ as synthesized in Example 24.

EXAMPLE 31

Synthesis of

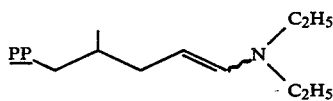

A nitrogen-purged three-necked flask was charged with 7.5 mg of Rh[(BINAP)(1,5-cyclooctadiene)]ClO$_4$, the catalyst was dissolved by adding 5 ml of anhydrous tetrahydrofuran, and then a solution of 0.85 g of the polyprenylamine of formula (I-14) in which n=15 and R$^3$=R$^4$=C$_2$H$_5$ (synthesized in Example 23) in 5 ml of anhydrous tetrahydrofuran was added. The mixture was heated with stirring at 60° C. for 20 hours under a nitrogen atmosphere. After cooling, 5 mg of (C$_6$H$_5$)$_2$PCH$_2$CH$_2$P(C$_6$H$_5$)$_2$ was added and the solvent was distilled off to give 0.85 g of an oil. Based on the analytical data shown below, this oil was identified as the polyprenyl compound of formula (I-16) in which n=15 and R$^3$=R$^4$=C$_2$H$_5$ IR analysis: 1660(shoulder), 1645, 1440, 1370, 1240, 1090, 930, 830 cm$^{-1}$.

$^1$H-NMR analysis: δ$_{CDCl_3}$$^{ppm}$ 0.93(d, 3H), 1.00(t, 6H), 1.53(s, 9H), 1.62(s, 48H), 1.7-2.3(73H), 2.88(q, 4H), 3.97(dd, 1H), 5.06(br, 18H), 5.76(d, 1H).

By essentially the same procedure as above, species of the polyprenyl compound of formula (I-16) in which R$^3$=R$^4$=C$_2$H$_5$ and n=11, 12, 13, 14, 16, 17, 18 and 19, respectively, were synthesized from corresponding polyprenylamine species of formula (I-14) in which R$^3$=R$^4$=C$_2$H$_5$ and n=11-19 but other than 15. For each of the species of formula (I-16), the characteristic absorptions on its infrared absorption spectrum and the characteristic signals on its $^1$H-NMR spectrum were in good agreement with those of the above-mentioned polyprenyl compound with respect to the positions of absorptions and signals.

EXAMPLES 32-37

Using 1.32 g (1 mmol) of the polyprenylcarboxylic acid of formula (I-4) in which n=15 as synthesized by the procedure of Example 7 and the amine of formula (IX) or (X) (1 mmole) and essentially following the procedure of Example 23, the corresponding amine of formula (I-14) or (I-15), respectively, was synthesized, and said amine was further converted to the corresponding polyprenyl compound of formula (I-16) or (I-17), respectively, by following the procedure of Example 31 except that, in Examples 36 and 37, the temperature of hydrogen shift was 40° C. The substituents R$^3$, R$^4$ and R$^5$ in the starting amines used are indicated below with the yields of the polyprenyl compounds of formula (I-16) and (I-17).

| Example No. | Amine of formula (IX) R$^3$ | R$^4$ | Polyprenyl compound of formula (I-16) Yield (g) |
|---|---|---|---|
| 32 | CH$_3$ | CH$_3$ | 0.87 |
| 33 | n-C$_4$H$_9$ | n-C$_4$H$_9$ | 0.94 |
| 34 | —(CH$_2$)$_4$— | | 0.85 |
| 35 | C$_6$H$_5$CH$_2$ | C$_6$H$_5$CH$_2$ | 0.92 |

| Example No. | Amine of formula (X) R$^5$ | Polyprenyl compound of formula (I-17) Yield (g) |
|---|---|---|
| 36 | C$_6$H$_5$ | 0.08 |
| 37 | cyclo-C$_6$H$_{11}$ | 0.84 |

The analytical data for each of the above polyprenyl compounds are shown below:

Enamine of Example 32 (R$^3$=R$^4$=CH$_3$)

IR analysis: 1660(shoulder), 1650, 1440, 1370, 1065, 930, 830 cm$^{-1}$.

$^1$H-NMR analysis: δ$_{CDCl_3}$$^{ppm}$ 0.91(d, 3H), 1.55(s, 9H), 1.63(s, 48H), 1.7-2.3(73H), 2.50(s, 6H), 4.03(dd, 1H), 5.06(br, 18H), 5.80(d, 1H).

Enamine of Example 33 (R$^3$=R$^4$=n—C$_4$H$_9$).

IR analysis: 1660(shoulder), 1645, 1440, 1370, 1240, 1090, 930, 830 cm$^{-1}$.

$^1$H-NMR analysis: δ$_{CDCl_3}$$^{ppm}$ 3.96(dd, 1H), 5.06(br, 18H), 5.75(d, 1H).

Enamine of Example 34 [R$^3$+R$^4$=-(CH$_2$)$_4$-].

IR analysis: 1660(shoulder), 1645, 1440, 1370, 1240, 1090, 930, 830 cm$^{-1}$.

$^1$H-NMR analysis: δ$_{CDCl_3}$$^{ppm}$ 0.93(d, 3H), 1.5-2.3(134H) including 1.53(s) and 1.62(s), 2.6-3.1(m, 4H), 3.96 (dd, 1H), 5.05(br, 18H), 5.76(d, 1H).

Enamine of Example 35 (R$^3$=R$^4$=CH$_2$C$_6$H$_5$).

IR analysis: 1660(shoulder), 1645, 1600, 1500, 1440, 1370, 930, 830, 750, 690 cm$^{-1}$.

$^1$H-NMR analysis: $\delta_{CDCl_3}^{ppm}$ 1.5–1.8(60H), 1.8–2.2(73H), 3.60(s, 4H), 3.96(dd, 1H), 5.06(br, 18H), 5.76(d, 1H), 7.1–7.6(m, 10H).

Imine of Example 36 ($R_5=C_6H_5$).

IR analysis: 1660(shoulder), 1645, 1595, 1440, 1370, 830, 750, 695 cm$^{-1}$.

$^1$H-NMR analysis: $\delta_{CDCl_3}^{ppm}$ 0.85–2.6(135H) including 1.53(s) and 1.62(s), 5.06(br, 18H), 6.3–7.3(m, 5H), 7.83(m, 1H).

Imine of Example 37 ($R^5$=cyclo—$C_6H_{11}$).

IR analysis: 1660, 1440, 1370, 830 cm$^{-1}$.

$^1$H-NMR analysis: $\delta_{CDCl_3}^{ppm}$ 5.06(br, 18H), 7.23(m, 1H).

Whereas, in the above Examples 32–37, the production and physical characteristics of the polyprenyl compounds of formulas (I-16) and (I-17) in which n=15 has been described, there were also synthesized those polyprenyl compound species of formulas (I-16) and (I-17) in which $R^3$ and $R^4$, and $R^5$ were the same as in Examples 32–37 and n=11, 12, 13, 14, 16, 17, 18 and 19 from polyprenylcarboxylic acid species of formula (I-4) in which n=11–19 but other than 15 on one hand and the same amines as used in Examples 32–37 by essentially following the procedure of Examples 32–37. For the product species, the characteristic absorptions on their infrared absorption spectra and the characteristic signals on their $^1$H-NMR spectra were in good agreement with those of the corresponding polyprenyl compounds in which n=15 as synthesized in Examples 32–37 with respect to the positions of the absorptions and signals.

EXAMPLE 38

Synthesis of

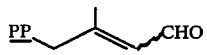

In 7.5 ml of dimethylformamide, there were dissolved 1.92 g of the polyprenylacetone of formula (I-1) in which n=15 (synthesized by essentially following the procedure of Example 1) and 1.0 g of 1,3-dioxan-2-ylmethyltriphenylphosphonium bromide (Wittig reagent; dried at 60° C./1 mmHg for 2 hours immediately before use). A lithium methoxide solution prepared from 16 mg of lithium and 7.5 ml of methanol was added dropwise over an hour with heating at 80°–90° C. under a nitrogen atmosphere. After the addition, the temperature was maintained at 80°–90° C. for further 2 hours with occasional checking of the progress of reaction by thin layer chromatography. Since the reaction was completed, the reaction mixture was poured into water and extracted sufficiently with hexane, the hexane layer was washed with an aqueous sodium chloride solution and dried over magnesium sulfate, and the solvent was distilled off using a rotary evaporator. The thus-obtained oil was dissolved in 15 ml of tetrahydrofuran, 5 ml of 10% hydrochloric acid was added, and the mixture was stirred at room temperature for 5 hours and, after dilution with 50 ml of water, extracted with hexane. The organic layer was washed in sequence with water, aqueous sodium bicarbonate and aqueous sodium chloride and dried over magnesium sulfate, the solvent was distilled off using a rotary evaporator, and the thus-obtained yellow oil was purified by silica gel column chromatography [developing solvent:hexane-ethyl acetate=97:3 (by volume)] to give 1.28 g of a colorless oil. Based on the analytical data shown below, this oil was identified as the polyprenylaldehyde of formula (I-18) in which n=15.

IR analysis: 2720, 1675, 1630, 1440, 1370, 1080, 830 cm$^{-1}$.

NMR analysis: $\delta_{CCl_4}^{ppm}$ 5.06(br, 18H), 5.75(d, 1H), 9.85 (d, 1H).

FD-MASS analysis: m/e=1308.

Essentially following the above procedure, polyprenylaldehyde species of formula (I-18) in which n=11–19 but other than 15 were synthesized from polyprenylacetone species of formula (I-1) having corresponding values of n (synthesized by essentially following the procedure of Example 1). The characteristic absorptions on their IR spectra and the characteristic signals on their NMR spectra were in substantial agreement, in the positions of the absorptions and signals, with those of the above-mentioned polyprenylaldehyde of formula (I-18) in which n=15. FD-MASS analysis gave the following data.

| Starting polyprenylacetone Value of n in formula (I-1) | Product polyprenylaldehyde Value of m/e |
|---|---|
| 11 | 1036 |
| 12 | 1104 |
| 13 | 1172 |
| 14 | 1240 |
| 16 | 1376 |
| 17 | 1444 |
| 18 | 1512 |
| 19 | 1580 |

EXAMPLE 39

Synthesis of

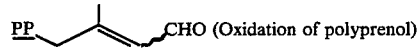

In a mixed solvent composed of 20 ml of hexane and 20 ml of diethyl ether, there was dissolved 4.0 g of the polyprenol of formula (V) in which n=15, then 14.5 g of activated manganese dioxide was added, and the mixture was stirred vigorously at room temperature for 7 hours. Thereafter, the mixture was filtered through a glass filter, the solid residue was washed well with hexane, the filtrate and the washings were combined, the solvent was distilled off using a rotary evaporator, and 4.0 g of the oil thus-obtained was purified by silica gel column chromatography [developing solvent:hexane-ethyl acetate=100:2 (by volume)] to give 3.1 g of a colorless oil. Based on the analytical data shown below, this product was identified as the polyprenylaldehyde of formula (I-18) in which n=14.

IR analysis: 2720, 1675, 1630, 1440, 1370, 1080, 830 cm$^{-1}$.

NMR analysis: $\delta_{CCl_4}^{ppm}$ 5.06(br, 17H), 5.76(d, 1H), 9.85(d, 1H).

FD-MASS analysis: m/e=1240.

Essentially following the above procedure, polyprenol species of formula (V) in which n=12–19 but other than 15 were oxidized to give corresponding polyprenylaldehyde species of formula (I-18) in which n=11–18 but other than 14, with yields comparable to the yield attained in the synthesis of the polyprenylaldehyde of formula (I-18) in which n=14. The characteristic absorptions on their IR spectra and the characteristic signals on their NMR spectra were in substantial agreement, in the positions of the absorptions and signals, with those of the above-mentioned polyprenylaldehyde of formula (I-18) in which n=14.

EXAMPLE 40

Synthesis of dolichol

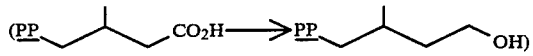

A three-necked flask was charged with 30 ml of anhydrous tetrahydrofuran and 380 mg of lithium aluminum hydride, the contents were cooled to 0° C. under a nitrogen atmosphere, a solution of 4.42 g of the dihydropolyprenylcarboxylic acid of formula (I-5) in which n=15 (synthesized by the procedure of Example 8) in 15 ml of anhydrous tetrahydrofuran was added dropwise with stirring. After the addition, the mixture was stirred at 0° C. for an hour and then at room temperature for 5 hours and poured portionwise into diluted hydrochloric acid, followed by good stirring. Hexane was added, the phases were separated, the aqueous layer was further extracted with two portions of hexane, the organic layers were combined and washed with aqueous sodium bicarbonate and saturated aqueous sodium chloride and dried over anhydrous magnesium sulfate, and the solvent was distilled off to give 4.12 g of a colorless oil. Purification of the oil by silica gel column chromatography [developing solvent:hexane-ethyl acetate=90:10 (by volume)] gave 3.82 g of a colorless oil. Based on the analytical data shown below, this product was identified as dolichol of general formula (XIII) in which n=15.

IR analysis: 3320, 2920, 2850, 1440, 1376, 1060, 830 cm$^{-1}$.

$^1$H-NMR analysis: $\delta_{CCl_4}^{ppm}$ 0.91(d, 3H), 1.60(s, 9H), 1.68(s, 48H), 1.10–1.80(m, 5H), 2.03(b, 70H), 3.66(m, 2H), 5.10(b, 18H).

$^{13}$C-NMR (ppm/intensity): 16.006/640, 17.679/353, 19.557/548, 23.430/6330, 25.308/567, 25.677/542, 26.436/5166, 26.699/548, 26.825/492, 29.316/528, 32.021/456, 32.245/5500, 37.548/582, 39.757/683, 40.029/541, 61.241/551, 124.214/445, 124.282/463, 124.448/505, 124.993/499, 125.071/5242, 131.210/213, 134.937/290, 135.005/349, 135.229/3567, 135.365/430.

FD-MASS: m/e=1312.

Essentially following the above procedure, dolichol species of general formula (XIII) in which n=11–19 but other than 15 were synthesized from dihydropolyprenylcarboxylic acid species of formula (I-5) having corresponding values of n with yields comparable to that attained in the synthesis of the dolichol species of n=15. The characteristic absorptions on their infrared absorption spectra and the characteristic signals on their $^1$H-NMR spectra were in substantial agreement, in the positions of the absorptions and signals, with those of the above-mentioned dolichol of n=15.

FD-MASS analysis gave the following data:

| Starting polyprenylcarboxylic acid Value of n in formula (I-5) | Product dolichol Value of m/e |
|---|---|
| 11 | 1040 |
| 12 | 1108 |
| 13 | 1176 |
| 14 | 1244 |
| 16 | 1380 |

-continued

| Starting polyprenylcarboxylic acid Value of n in formula (I-5) | Product dolichol Value of m/e |
|---|---|
| 17 | 1448 |
| 18 | 1516 |
| 19 | 1584 |

EXAMPLE 41

Synthesis of dolichol

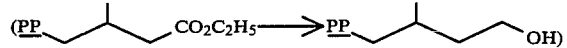

A three-necked flask was charged with 20 ml of anhydrous diethyl ether and 200 mg of lithium aluminum hydride, the contents were cooled to 0° C. under a nitrogen atmosphere, and a solution of 3.39 g of the ethyl dihydropolyprenylcarboxylate of formula (I-3) in which n=15 and $R^6$=C$_2$H$_5$ (synthesized by the procedure of Example 11) in 10 ml of anhydrous diethyl ether was added dropwise with stirring. After completion of the addition, the mixture was stirred overnight at room temperature and then thereto were added dropwise carefully with vigorous stirring 0.2 ml of water, 0.2 ml of 15% aqueous sodium hydroxide and 0.6 ml of water in that order. The resulting white granular precipitate was filtered off, the organic layer was dried over anhydrous magnesium sulfate, the solvent was distilled off, and the thus-obtained colorless oil (3.25 g) was purified by silica gel column chromatography [developing solvent:hexane-ethyl acetate=90:10 (by volume)] to give 3.03 g of dolichol of general formula (XIII) in which n=15. The results of IR analysis, NMR analysis and FD-MASS analysis of this product were in good agreement with those of the dolichol of n=15 obtained in Example 40.

Essentially following the above procedure, dolichol species of general formula (XIII) in which n=11–19 but other than 15 were synthesized from ethyl dihydropolyprenylcarboxylate species of formula (I-3) having corresponding n values with $R^6$=C$_2$H$_5$. The yields were almost the same as in the case of the synthesis of dolichol with n=15. The results of IR analysis, NMR analysis and FD-MASS analysis were in good agreement with those of the dolichol species obtained in Example 40 and having corresponding values of n.

EXAMPLE 42

Synthesis of dolichol

[PP⌇⌇⌇N(C$_2$H$_5$)$_2$⟶

PP⌇⌇⌇CHO⟶PP⌇⌇⌇OH]

In 30 ml of tetrahydrofuran was dissolved 0.80 g of the polyprenyl compound of formula (I-16) in which n=15 and $R^3$=$R^4$=C$_2$H$_5$ (synthesized in Example 31), then 10 ml of 10% hydrochloric acid was added, and the mixture was stirred at room temperature for 3 hours. Thereafter, 100 ml of water was added and the mixture was extracted with three portions of hexane. The organic layers were combined, washed with water, aqueous sodium bicarbonate and saturated aqueous sodium chloride and then dried over anhydrous magnesium sulfate, and the solvent was distilled off. The thus-obtained yellow oil (0.72 g) was purified by silica gel column chromatography [developing solvent:hexane-ethyl acetate=90:10 (by volume)] gave 0.63 g of a colorless oil. Based on the analytical data shown below, the product was identified as the polyprenylaldehyde of formula (XI) in which n=15.

IR analysis: 3060(weak), 2950, 2910, 2850, 2730(weak), 1725, 1660, 1440, 1375, 830 cm$^{-1}$.

$^1$H-NMR analysis: $\delta_{CCl_4}{}^{ppm}$ 0.91(d, 3H), 1.60(s, 9H), 1.68(s, 48H), 5.05(b, 18H), 9.70(t, 1H).

FD-MASS analysis: m/e=1310.

The above polyprenylaldehyde (0.60 g) was dissolved in 5 ml of hexane, then 2.5 ml of ethanol was added, the mixture was cooled on an ice water bath with stirring, and 0.1 g of sodium borohydride was added. After allowing the reaction to proceed for an hour, a saturated aqueous ammonium chloride solution was added. After addition of water, the hexane layer was separated, and the aqueous layer was extracted with two portions of hexane. The organic layers were combined, washed with saturated aqueous sodium chloride and dried over anhydrous magnesium sulfate, and the solvent was distilled off. The thus-obtained colorless oil (0.58 g) was purified by silica gel column chromatography [developing solvent:hexane-ethyl acetate=90:10 (by volume)] to give 0.52 g of dolichol [general formula (XIII), n=15]. The results of IR analysis, NMR analysis and FD-MASS analysis were in good agreement with those of the dolichol of n=15 obtained in Example 40.

Essentially following the above procedure, dolichol species of general formula (XIII) in which n=11-19 but other than 15 were synthesized from polyprenyl compound species of formula (I-16) having corresponding values of n with R$^3$=R$^4$=C$_2$H$_5$, with comparable yields to that attained in the synthesis of the dolichol of n=15. The results of IR analysis, NMR analysis and FD-MASS analysis were in good agreement with those of the dolichol species obtained in Example 40 and having corresponding values of n.

What we claim is:

1. A polyprenyl compound represented by the fomrrula

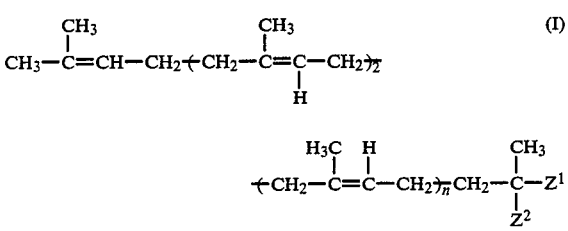

wherein

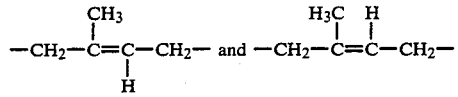

represent a trans-isoprene unit and a cis-isoprene unit, respectively, n is an integer of 11 to 19, and Z$^1$ and Z$^2$ combinedly represent =O, =CH—COOH, =CH—COOR$^1$, =CH—CN, =C(CN)COOR$^2$, =CH—CO—NH$_2$, =CH—CO—N(R$^3$)(R$^4$), =CH—CO—NHR$^5$, =CH—CH$_2$—N(R$^3$)(R$^4$), =CH—CH$_2$—NHR$^5$ or =CH—CHO or Z$^1$ is a hydrogen atom and Z$^2$ is —CH$_2$COOH, —CH$_2$COOR$^6$, —CH(CN)COOR$^2$, —CH$_2$CN, —CH$_2$—CO—NH$_2$, —CH=CH—N(R$^3$)(R$^4$) or —CH$_2$—CH=N—R$^5$, R$^1$, R$^2$ and R$^6$ each being a lower alkyl group, R$^3$ and R$^4$ each being independently a lower-alkyl, cycloalkyl, aryl or aralkyl group or R$^3$ and R$^4$ combinedly representing an alkylene group containing 2 to 5 carbon atoms, and R$^5$ being a lower-alkyl, cycloalkyl, aryl or aralkyl group.

2. The polyprenyl compound of claim 1, which is represented by the formula

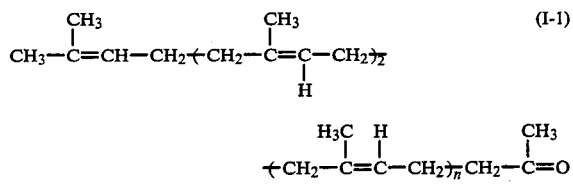 (I-1)

wherein

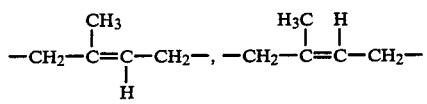

and n are as defined in claim 1.

3. The polyprenyl compound of claim 1, wherein Z$^1$ and Z$^2$ combinedly represent =CH—COOH or =CH—COOR$^1$ in which R$^1$ is as defined in claim 1.

4. The polyprenyl compound of claim 1, wherein Z$^1$ is a hydrogen atom and Z$^2$ is —CH$_2$COOH or —CH$_2$COOR$^6$ in which R$^6$ is as defined in claim 1.

5. The polyprenyl compound of claim 1, wherein Z$^1$ and Z$^2$ combinedly represent =CH—CN or =CH—CO—NH$_2$.

6. The polyprenyl compound of claim 1, wherein Z$^1$ is a hydrogen atom and Z$^2$ is —CH$_2$CN or —CH$_2$—CO—NH$_2$.

7. The polyprenyl compound of claim 1, wherein Z$^1$ and Z$^2$ combinedly represent =CH—CO—N(R$^3$)(R$^4$), =CH—CO—NH(R$^5$), =CH—CH$_2$—N(R$^3$)(R$^4$) or =CH—CH$_2$—NHR$^5$ in which R$^3$, R$^4$ and R$^5$ are as defined in claim 1.

8. The polyprenyl compound of claim 1, wherein Z$^1$ is a hydrogen atom and Z$^2$ is —CH=CH—N(R$^3$)(R$^4$) or —CH$_2$—CH=N—R$^5$ in which R$^3$, R$^4$ and R$^5$ are as defined in claim 1.

9. The polyprenyl compound of claim 1, wherein Z$^1$ and Z$^2$ combinedly represent =CH—CHO.

10. The polyprenyl compound of claim 1, wherein n is 15.

* * * * *